(12) United States Patent
Das et al.

(10) Patent No.: US 8,551,784 B2
(45) Date of Patent: Oct. 8, 2013

(54) CIS DI-AHL MODIFIED CONTROLS FOR GLYCATED HEMOGLOBIN S-A1C DERIVED FROM HEALTHY BLOOD CELLS

(75) Inventors: Kausik Das, Lincoln, NE (US); Gary D. Krzyzanowski, Omaha, NE (US)

(73) Assignee: Streck, Inc., LaVista, NE (US)

( * ) Notice: Subject to any disclaimer, the term of this patent is extended or adjusted under 35 U.S.C. 154(b) by 0 days.

(21) Appl. No.: 13/299,058

(22) Filed: Nov. 17, 2011

(65) Prior Publication Data

US 2012/0122073 A1     May 17, 2012

Related U.S. Application Data

(60) Provisional application No. 61/414,621, filed on Nov. 17, 2010, provisional application No. 61/414,631, filed on Nov. 17, 2010, provisional application No. 61/414,633, filed on Nov. 17, 2010.

(51) Int. Cl.
   *G01N 31/00*    (2006.01)
(52) U.S. Cl.
   USPC .............................................. 436/14; 435/13
(58) Field of Classification Search
   None
   See application file for complete search history.

(56) References Cited

U.S. PATENT DOCUMENTS

| | | | |
|---|---|---|---|
| 4,675,185 A * | 6/1987 | Kandler et al. | 424/93.73 |
| 5,196,182 A | 3/1993 | Ryan | |
| 5,262,327 A | 11/1993 | Ryan | |
| 5,460,797 A | 10/1995 | Ryan | |
| 5,529,933 A | 6/1996 | Young et al. | |
| 5,811,099 A | 9/1998 | Ryan | |
| 5,849,517 A | 12/1998 | Ryan | |
| 5,858,790 A | 1/1999 | Kim et al. | |
| 6,187,590 B1 | 2/2001 | Kim et al. | |
| 6,221,668 B1 | 4/2001 | Ryan et al. | |
| 6,890,756 B2 | 5/2005 | Wu | |
| 7,247,484 B2 | 7/2007 | Wu et al. | |
| 7,361,513 B2 | 4/2008 | Ryan et al. | |
| 2005/0175977 A1 * | 8/2005 | Posner et al. | 435/2 |

OTHER PUBLICATIONS

Spicer et al. "Synthesis of Hemoglobin A1c and related minor hemoglobins by erythrocytes." (1979) Journal of Clinical Investigation, vol. 64, 40-48.*
Chandalia and Krisnaswamy, "Glycated Hemoglobin" (2002) Current Science, vol. 83, No. 12, 1522-1532.*
"Position Statement: Test of Glycemia in Diabetes" (2003) Diabetes Care, vol. 26, Supp. 1, S106-S108.*
Bridges et al. "The acetylation of hemoglobin by aspirin. In vitro and in vivo." (1975) Journal of Clinical Investigation, vol. 56, 201-207.*
Position Statement, "Aspirin Therapy in Diabetes." (2004) American Diabetes Association, vol. 27, S72-S73.*

* cited by examiner

*Primary Examiner* — Ralph Gitomer
*Assistant Examiner* — Teresa E Knight
(74) *Attorney, Agent, or Firm* — The Dobrusin Law Firm, PC

(57) ABSTRACT

The invention is composition comprising red blood cells in an aqueous suspension medium and one or more cis di-ahls; wherein more than 6 percent by weight of the hemoglobin in the red blood cells is S-A1c glycated hemoglobin. In another embodiment, the invention is a method comprising contacting red blood cells in a suspension medium having a concentration of S-A1c glycated hemoglobin of greater than 6 percent by weight of the hemoglobin in the red blood cells with a sufficient amount of one or more cis di-ahls such that the concentration of S-A1c glycated hemoglobin in resulting composition as measured by high pressure liquid chromatography, immunoassay and boronate affinity methods is consistent.

18 Claims, No Drawings

US 8,551,784 B2

CIS DI-AHL MODIFIED CONTROLS FOR GLYCATED HEMOGLOBIN S-A1C DERIVED FROM HEALTHY BLOOD CELLS

CLAIM OF PRIORITY

This application claims priority from provisional application Ser. No. 61/414,621 filed Nov. 17, 2010; provisional application Ser. No. 61/414,631 filed Nov. 17, 2010 and provisional application Ser. No. 61/414,633 filed Nov. 17, 2010 all incorporated herein by reference in their entirety.

FIELD OF THE INVENTION

This invention relates generally to compositions derived from healthy red blood cells containing S-A1c glycated hemoglobin and cis di-ahls, methods of preparing these compositions, controls containing these compositions wherein the controls are useful to calibrate analytical instruments used to determine the amount of glycated hemoglobin contained in blood samples. The present invention relates to control compositions and the manufacture and use of the same pursuant to which the red blood cells of the control (e.g., red blood cells obtained from whole blood of a donor who need not be diabetic) are processed in a manner for realizing simulated red blood cells, in relevant characteristics, of a diabetic person so that when analyzed by an instrument capable of detecting such characteristics, the instrument detects such characteristics. Even more specifically the simulated red blood cells are such that they include glycosolated hemoglobin, which is contained in a sealed cell membrane, and which is a result of A1c synthesis that occurs within the membrane.

BACKGROUND OF THE INVENTION

In the diagnosis, treatment and management of patients with diabetes, sensitive instruments are employed for detecting one or more measurable characteristics of a patient blood sample. In a clinical laboratory environment there is a need to ensure that such instruments are performing properly. The use of control compositions having known characteristics is an accepted way to assure proper instrument performance. Though it is possible to use human whole blood as a control, it is not desirable due to stability considerations as well as availability. For example, in this context there would be a need for a ready supply of fresh diabetic whole blood. Another accepted approach is to synthesize a control composition that simulates relevant detectable characteristics measured by an instrument. An approach to one such synthetic control composition is illustrated in U.S. Pat. No. 7,361,513 (Ryan). Though such an approach yields useful control compositions, there remains a need for other such compositions. For example, there has been a longstanding need for a control that does not require diabetic blood as a starting material, that employs A1c synthesis entirely within a cell membrane, or any combination thereof. There is also a need for achieving a control that has in-situ synthesized A1c contained within a membrane in an amount of a nature so that it is detectable as such by a number of different instruments which may employ differing detection strategies. Hemoglobin (Hb) is a respiratory molecule found in red blood cells. It is responsible for transporting oxygen from the lungs to body cells and for transporting carbon dioxide from body cells to the lungs. Hemoglobin may be modified by the free glucose present in human plasma to form glycated hemoglobin (GHB). Hemoglobin A1c (Hb A1c, also referred to as A1c), constituting approximately 80 percent of all glycated Hb, is generated by the spontaneous reaction of glucose with the N-terminal amino group of the Hb A beta chain. The Hb A1c and the total glycated Hb values have a high degree of correlation, and either value may be used, for example in the management of treating diabetes. Formation of Hb A1c is slow but irreversible, and the blood level depends on both the life span of the red blood cells (average 120 days) and the blood glucose concentration. Therefore, Hb A1c represents the time-averaged blood glucose values over the preceding 2 to 3 months, and is not subject to wide fluctuations observed in blood glucose values. With respect to diabetes management, studies have shown that quality of life improves with decreasing levels of Hb A1c, and measurements every 3 to 6 months are recommended.

The determination of total hemoglobin is indicative of the oxygen-carrying capacity of whole blood. The numerous methods and devices for the determination of hemoglobin include both direct analysis, i.e., analysis without prior modification of the hemoglobin, and indirect analysis. It is important to accurately determine the total hemoglobin in the Hb A1c assay, because A1c is often reported as a fraction of the total hemoglobin. Multiple Hb A1c assay methodologies have been developed since late 1970s. One of the standard methods for measuring Hb A1c uses ionic-exchange high performance liquid chromatography (HPLC), which separates and analyzes Hb A1c and other minor Hb components from unmodified hemoglobin (Hb A0) based upon their differences in chemical charges. A second methodology for detection of Hb A1c is designed by immunoinhibition turbidimetric techniques. The Hb A1c assay in immunoassay includes an antibody-antigen reaction and a following turbidity measurement. The third methodology is boronate affinity chromatography, which utilizes a gel matrix containing immobilized boronic acid to capture the cis-diol group of glycated hemoglobin. The variety of Hb A1c testing methodologies requires a novel control that could be used in various methods and devices for detecting Hb A1c levels. In most of the available methods, the first step for measuring Hb A1c levels is the manual or automatic production of a hemolysate by lysing the red blood cells with a special lytic reagent. Therefore, there is an ongoing need for cellular Hb A1c standards or controls that exhibit a similar matrix to that of patient specimens and that function in the analytical testing phases during an Hb A1c assay.

Currently, there are a number of Hb A1c normal and abnormal controls on the market. Some of these controls are disclosed in Wu et. al. U.S. Pat. No. 7,247,484 B2; Wu U.S. Pat. No. 6,890,756 B2; Posner et. al. US Patent Publication 2005/0175977; and Ryan et al. U.S. Pat. No. 7,361,513 B2; all incorporated herein by reference. The A1c-Cellular control preparation described in U.S. Pat. No. 7,361,513 begins by selection of red blood cells from a suitable subject. The Level 1 (lower or normal level) is described to be manufactured by utilizing the red blood cells obtained from a healthy donor with an A1c≤6%. The Level 2 (higher or diabetic level) was described to be manufactured by utilizing the red blood cells obtained from known diabetic donor with an A1c≥9%. The suitable red blood cells were then stabilized and preserved for long term stability. However, manufacturing diabetic level A1c control using the diabetic blood samples, obtained from diabetic donors suffer a number of serious draw backs. These drawbacks include both inferior quality and insufficient quantity of diabetic blood samples, as well as economical disadvantages. Obtaining natural diabetic blood from diabetic patients is restricted. Therefore, obtaining sufficient amount of natural diabetic blood to meet the growing manufacturing volume of A1c control has become an increasing challenge.

The availability of diabetic blood sample with a definite range of A1c value is even more difficult. Red Cross eligibility for blood donation states that diabetic individuals can donate blood only if the individual is under treatment and the situations are under control. The A1c values of blood samples obtained from diabetic patients are also inconsistent. According to the American Diabetic Association, any individual with A1c≥6.5 is identified as diabetic. The A1c values of blood samples from diabetic patients may vary from 6.5 to as high as ~30.0. Further, the lot-to-lot variability of the A1c values of the A1c controls manufactured by mixing these blood samples are extremely high. In other words, different lots of the diabetic level of A1c control may have significantly different A1c values. This inconsistency is much less in the case of normal level due to abundance of blood sample with A1c≈5-6% range. The A1c values of the blood sample obtained from diabetic patient may appear falsely elevated or decreased if the blood of the individual donor contains any abnormal hemoglobin variant. A number of clinical studies reported that the presence of abnormal hemoglobin variants influences A1c values of healthy and diabetic patients, see Bry L, Chen P C, Sacks D B. Effects of hemoglobin variants and chemically modified derivatives on assays for glycohemoglobin. Clin Chem. 2001; 47: 153-163. In general, ion exchange chromatographic and gel electrophoresis methods are affected more than the immunoassay or affinity based methods. In case of ion exchange chromatographic method, when the abnormal variant co-elutes with Hb-A1c, then an increase in A1c value is observed. If the abnormal variant co-elutes with A0 (normal hemoglobin), then an apparent decrease in A1c value is observed. Therefore, manufacturing A1c control using blood from a donor with unknown hemoglobin composition may cause serious risk in the accuracy of the A1c values. Rey et al. reported presence of Hb Seville[$\alpha_2\beta_2 81$(EF5) Leu→Phe] causes falsely low A1c value when measured on ion-exchange chromatography, see Rey T H del, Conde-Sanchez M, Ropero-Gradilla P et al. Hemoglobin Seville [$\alpha_2\beta_2 81$(EF5)Leu→Phe] a silent phenotypic variant that interferes in hemoglobin A1c measurement by ion-exchange HPLC method. Clin Biochem. 2011; 44: 933-935. Bergman et al. demonstrated that presence of Hb Stockholm [$\beta 7$(A4) Glu→Asp] causes falsely low A1c value on Variant II™ chromatography system, see Bergman A C, Beshara S, Byman I, Karim R, Landin B. A new β-chain variant: Hb Stockholm [($\beta 7$(A4)Glu→Asp] causes falsely low HbA1c. Hemoglobin. 2009; 33: 137-142. Friess et al. reported that the presence of a novel hemoglobin variant [$\beta 66$(E10)Lys→Asn] causes a falsely low A1c value measured on cation exchange Tosoh 2.2, see Friess U, Beck A, Kohne E. et al. Novel hemoglobin variant [$\beta 66$(E10)Lys→Asn], with decreased oxygen affinity, causes falsely low hemoglobin A1c values by HPLC. Clin Chem. 2003; 49: 1412-1415. Chen et. al reported that the Hb-Raleigh [$\beta 1$Val→Ala] causes false increase in A1c value on ion-exchange, see Chen D, Crimmins D L, Hsu F F, et al. Hemoglobin Raleigh as the cause of a falsely increased hemoglobin A1c in an automated ion-exchange HPLC method. Clin Chem. 1998; 44: 1296-1301. Zhu et al. demonstrated that the presence of HbS in S-$\beta^+$-thalassemia causes a false A1c values on Bio-Rad Variant II Turbo, see Zhu Y, Williams L M. Falsely elevated hemoglobin A1c due to S-$\beta^+$-thalassemia interference in Bio-Rad Variant II Turbo HbA1c assay. Clin Chim Acta. 2009; 409: 18-20. Frers et al. observed falsely increased A1c values by HPLC based Tosoh 2.2 for a blood sample that contained Hb Okayama [$\beta 2$(NA2)His→Gln], see Frers C R, Dorn S, Schmidt W. et al. Falsely increased HbA1c values by HPLC and falsely decreased values by immunoassay lead to identification of Hb Okayama and help in the management of a diabetic patient. Clin Lab. 2000; 46: 569-573. Common hemoglobin variants such as Hb S, Hb J, Hb F or Hb E are also reported by Chu et al. to influence the A1c measurement by Tosoh G7 analyzer, Chu C H, Lam H C, Lee J K. et al. Common hemoglobin variants in southern Taiwan and their effect on the determination of HbA1c by ion-exchange high-performance liquid chromatography. J Clin Med Assoc 2009; 72: 362-367. Immunoassay method based A1c measurements are also known to be affected by the presence of abnormal hemoglobin variants when immune recognition sites of normal A1c or normal hemoglobin are modified by mutation, see Bry L et al, supra. Blood samples collected from the individuals diagnosed with different diseases are also reported to cause inaccurate A1c measurements. Consequently, A1c control manufactured by using blood samples collected from such patients can introduce a great deal of inconsistency in A1c values of the control product. Bannon et al.[11] and Engbaek et al.[12] reported falsely elevated A1c values measured by ion-exchange chromatography for the patients with uremia, see Bannon P, Lessard F, Lepage R. Glycated hemoglobin in uremic patients as measured by affinity and ion-exchange chromatography. Clin Chem. 1984; 30: 485-486 and Engbaek F, Christensen S E, Jespersen B. Enzyme immunoassay of hemoglobin A1c: Analytical characteristics and clinical performance for patients with diabetes mellitus, with and without uremia. Clin Chem. 1989; 35: 93-97. For such patients, carbamylated derivative of hemoglobin (hemoglobin+urea reaction product) co-elutes with hemoglobin A1c resulting an apparent increase in A1c value in ion-exchange chromatographic methods. Suzuki et al. reported an extremely high A1c value (21%) in a patient and reasoned the false increase in A1c is due to the acute lymphoblastic leukemia, see Suzuki Y, Shichishima T, Yamashiro Y. et al. A patient with acute lymphoblastic leukaemia presenting an extremely high level (21.0%) of HbA1c. Annals Clin Biochem. 2011; 48: 474-477. Danzig et al. reported that the type 1 diabetic patients with glucose-6-phosphatase dehydrogenase deficiency showed falsely decreased A1c values, see Danzig J A, Moser J T, Belfield P. et al. Glucose-6-phosphate dehydrogenase deficiency diagnosed in an adolescent with type 1 diabetes mellitus and hemoglobin A1c discordant with blood glucose measurement. J. Pediatrics 2011: 849-851. Several chemical agents used as drug may bind with hemoglobin variants which can affect A1c measurement. These hemoglobin-drug derivatives can co-elute with A1c in ion-exchange chromatography causing false result. Likewise, they can interfere with antibody recognition in immunoassay method or chemical recognition in affinity method yielding false results. Evidently, blood samples, obtained from the donors who are under treatment, are not suitable for manufacturing A1c control with a consistent A1c value. Aspirin has been identified by a number of researchers to cause false elevation of A1c values resulted from HPLC based analyzers. Aspirin (acetylsalicylic acid) binds with hemoglobin producing acetylated hemoglobin which co-elutes with A1c in HPLC chromatography resulting falsely elevated A1c, see Nathan D M, Francis T B, Palmer J L. Effect of Aspirin on determination of glycosylated hemoglobin. Clin Chem. 1983; 29: 466-469; Bridges K R, Schmidt G J, Jensen M. et al. The acetylation of hemoglobin by aspirin. In vitro and in vivo. J Clin Invest. 1975; 56:201-207; Camargo J L, Stifft J, Gross J L. The effect of aspirin and Vitamins C and E on HbA1c assays. Clin Chim Acta 2006; 372: 206-209; and Weykamp C W, Penders T J, Siebelder C W M, et al. Interference of carbamylated and acetylated hemoglobin in assays f glycohemoglobin by HPLC, electrophoresis, affinity chromatography and enzyme immunoassay. Clin Chem. 1993; 39: 138-142. Gross et al. identified ribavirin and peginterferon alfe-2b therapy for hepatitis C viral infection cause false lowering of A1c values, see Gross B N, Cross B, Foard J C, Falsely low hemoglobin A1c levels in a patient receiving ribavirin and peginerferon alfa-2b for hepatitis C. Pharmacotherapy, 2009; 29: 121-123. Brown et al. reported false low A1c level for the diabetic patients with chronic kidney disease who were undergoing erythropoietin therapy with epoetin alfa and darbepoetin alfa drugs, Brown J N, Kemp D W, Brice K R. Class effect of erythropoietin therapy on hemoglobin A1c in a patient with diabetes mellitus and chronic kidney disease not undergoing hemodialysis, Pharmacotherapy, 2009; 29:468-472. Vitamins C and E are also suggested to yield falsely decreased A1c values, see Suadek C D, Derr R L, Kalyani R R. Assessing glycemia in diabetes using self-monitoring blood glucose and hemoglobin A1c. Clin Rev. 2006; 295:1688-1697 and Schrot R J, Patel K T, Foulis P. Evaluation of inaccuracies in the measurement of glycemia in the laboratory, by glucose meters, and through measurement of hemoglobin A1c. Clin Diabetes 2007; 25: 43-49. Blood samples interact inconsistently with various analytical methods due to presence of different hemoglobin variants, chemical derivatives of hemoglobin or presence of drugs in the patient blood. A majority of these affect ion-exchange based chromatographic methods such as HPLC or electrophoresis. However, immunoassay and affinity based methods are also known to be affected, see Bry L, supra. Inconsistency of the blood samples for A1c control manufacturing can also be introduced by difference of the ages of the samples obtained. Due to the scarcity, diabetic blood samples might be collected as they become available. Therefore, the ages of the blood cells in a collection of blood packs might be different introducing inferior stability and inconsistent integrity of the cells. As the diabetic donors are rare, the prices of the diabetic blood samples are significantly greater than the normal blood samples.

The factors discussed above justify avoiding manufacture high level A1c control using natural diabetic blood. The factors also encourage to obtain healthy blood samples and biosynthetically convert it to a diabetic resembling blood sample with high A1c values. Such a conversion to synthetically increase hemoglobin A1c concentration by in vitro glycation of hemoglobin are known in literature, see Posner A H, Reichenbach D L, Hemoglobin isolation and preparation of glycosylated hemoglobin. US 2005/0175977; Bunn H F, Haney D N, Kamin S. et al. The biosynthesis of human hemoglobin A1c. J Clin Invest. 1976; 57: 1652-1659 and Spicer K M, Allen R C, Hallett D, Buse M G. Synthesis of hemoglobin A1c and related minor hemoglobins by erythrocytes. In vitro study of regulation. J. Clin Invest. 1979; 64: 40-48. However, these conversions were carried out either by pure hemoglobin or by erythrocyte hemolysate. Glycation of hemoglobin within intact red cells are unprecedented. Ryan et al. described two methods of in vitro glycations of hemoglobin with red cells which are less than ideal for manufacturing purpose.[1] The first method proposed by Ryan et al. described a reductive glycation of red blood

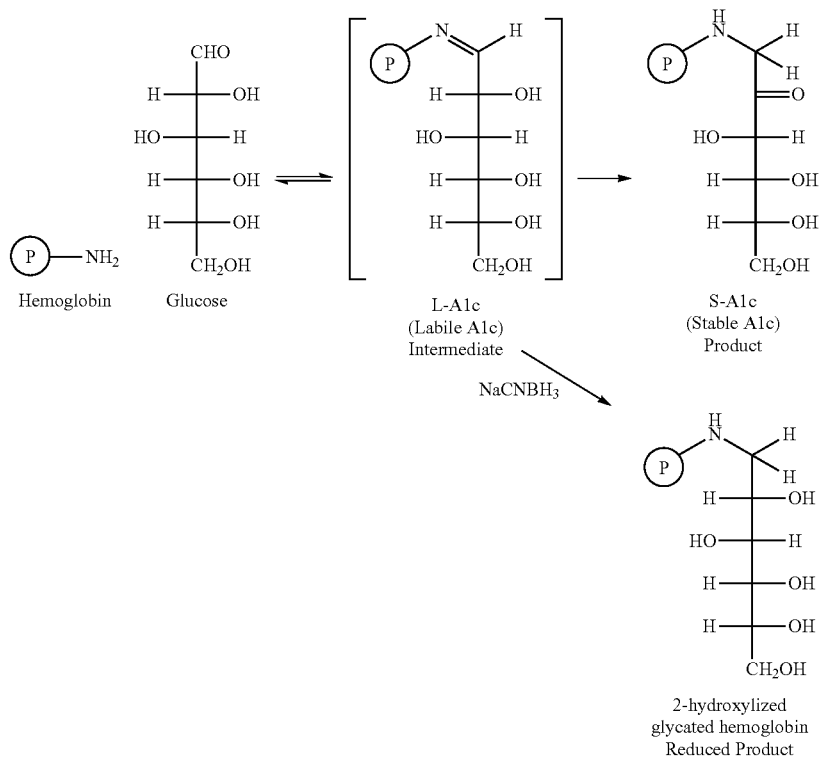

cells with 3% hemoglobin and 0.5% $NaCNBH_3$. This method yields 2-hydroxylized glycated hemoglobin which is not recognized as A1c by ion-exchange chromatographic or immunoassay methods. Ryan et al. also described slow synthesis of A1c by incubating red blood cells with ~3% glucose at 4-6° C. which takes ~50 days to achieve desired high concentration of A1c. It is desirable for efficient manufacturing to develop processes that can be performed faster.

Many prior art solutions require glycosylation outside of the blood cells which limit the usefulness of glycosylated materials in controls. Many A1c controls also fail to produce controls that resemble a true patient blood sample. Such controls cannot be utilized to create universal controls, or controls that test multiple parameters of a patient blood sample. The leakage of hemoglobin from the red blood cells may render the control ineffective for its intended use, thus requiring that the red blood cell membranes be preserved to prevent this undesirable leakage. This can render controls prepared form such red blood cells to not be stable for the desired time frame.

Unlike control products disclosed in the prior art, the present teachings allow for glycosylation to occur within the red blood cells so that the synthesis of A1c also occurs within the red blood cells. Unexpectedly, the present teachings include methods whereby the red blood cell membranes are preserved so that such synthesis occurs without damage to the cell membrane. As a further benefit of glycosylation within the red blood cells, the resulting control contains a more uniform population of glycosylated cells. Many A1c controls also fail to produce controls that resemble a true patient blood sample. Such controls cannot be utilized to create universal controls, or controls that test multiple parameters of a patient blood sample. The present teachings are directed to controls capable of testing multiple elements of a blood sample, which may include various white blood cell populations, nucleated red blood cells, reticulocytes or other blood cell types. In addition, the present teachings provide for one control product that produces consistent data for a number of hematology analyzers, as opposed to requiring a distinct control for each analyzer. As a further benefit of the present teachings, the preservation of the red blood cell membranes results in a shelf-stable product whereby the red blood cells resist hemoglobin leakage for a period of at least about 4 months, or longer. The leakage of hemoglobin from the red blood cells may render the control ineffective for its intended use, thus requiring that the red blood cell membranes be preserved to prevent this undesirable leakage. The present invention addresses one or more of the above needs by providing improved controls and methods for making the controls for testing the Hb A1c level in diabetic blood wherein the controls can be prepared in a reasonable time frame with good accuracy and precision and consistency among the standard methods.

SUMMARY OF THE INVENTION

The present invention addresses one or more of the above needs by providing improved methods for making the controls for testing the Hb A1c level in diabetic blood wherein the controls can be prepared to mimic relevant detectable characteristics of diabetic blood in a reasonable time frame with good accuracy and precision and at temperatures that do not result in hemolysis. The processing of red blood cells of a starting material can be performed in situ within a red blood cell membrane, and in a manner so that the membrane is substantially intact from its pre-processing state, thereby avoiding hemoglobin loss and maintaining storage stability (e.g., for a period of at least one week, two weeks, one month, two months, three months or longer). Controls according to aspects of the invention are useful in methods of comparing performance of an instrument against predetermined known values for the control. Such methods can be performed for a single instrument or across a plurality of different instruments. The present invention provides a unique control composition in that it employs as a starting material whole blood from a donor who need not be a diabetic. In fact, starting materials may be free of diabetic whole blood.

The present teachings allow for the for glycosylation of hemoglobin to occur within the red blood cells so that the synthesis of A1c also occurs within the red blood cells; methods whereby the red blood cell membranes are preserved so that such synthesis occurs without damage to the cell membrane; controls prepared from such glycosylated hemoglobin contains a more uniform population of glycosylated cells are capable of testing multiple elements of a blood sample, (which may include various white blood cell populations, nucleated red blood cells, reticulocytes or other blood cell types). In addition, the present teachings provide for one control product that produces consistent data for a number of hematology analyzers, as opposed to requiring a distinct control for each analyzer. The preservation of the red blood cell membranes results in a shelf-stable product whereby the red blood cells resist hemoglobin leakage for a period of at least about 4 months, or longer.

Unlike control products disclosed in the prior art, the present teachings allow for glycosylation to occur within the red blood cells so that the synthesis of A1c also occurs within the red blood cells. Unexpectedly, the present teachings include methods whereby the red blood cell membranes are preserved so that such synthesis occurs without damage to the performance of the cell membrane. As a further benefit of glycosylation within the red blood cells, the resulting control contains a substantially more uniform population of glycosylated cells. Many A1c controls also fail to produce controls that resemble a true patient blood sample. Such controls cannot be utilized to create universal controls, or controls that test multiple parameters of a patient blood sample. The present teachings are directed to controls capable of testing multiple elements of a blood sample, which may include various white blood cell populations, nucleated red blood cells, reticulocytes or other blood cell types. In addition, the present teachings provide for one control product that produces consistent data for a number of hematology analyzers, as opposed to requiring a distinct control for each analyzer. As a further benefit of the present teachings, the preservation of the red blood cell membranes results in a shelf-stable product whereby the red blood cells resist hemoglobin leakage and remain stable for an extended period of time that is significantly longer than the stability period for untreated human whole blood (e.g., for a period of at least about 4 months, or longer). The leakage of hemoglobin from the red blood cells may render the control ineffective for its intended use, thus requiring that the red blood cell membranes be preserved to prevent this undesirable leakage. The newly invented methods focused on the efficient manufacturing of blood samples with high A1c values from healthy blood samples with normal A1c values. These new methods are based on glycation of hemoglobin within intact red cells. These methods allow one to circumvent one or more difficulties associated with the processes described in the prior art. In vitro glycation can produce blood samples with high A1c values using healthy blood sample with normal A1c values which are abundant and free of drugs or drug derivatives of hemoglobin. As these normal blood samples are obtained from healthy individuals, they are usually free from interfering abnormal hemoglobin variants. Additionally the in vitro glycation method also provides other advantages. The primary advantage is to have control on the manufacturing process to obtain any amount of high A1c level glycated blood sample to meet the increasing demand. The standardized glycation method also allows the manufacturer to eliminate lot to lot variation of A1c values or blood cell count.

The invention provides a number of advantages over the prior art as described herein. Unlike control products disclosed in the prior art, the present teachings allow for glycosylation to occur within the red blood cells so that the synthesis of A1c also occurs within the red blood cells. Unexpectedly, the present teachings include methods whereby the red blood cell membranes are preserved so that such synthesis occurs without damage to the cell membrane. As a further benefit of glycosylation within the red blood cells, the resulting control contains a more uniform population of glycosylated cells. Many A1c controls also fail to produce controls that resemble a true patient blood sample. Such controls cannot be utilized to create universal controls, or controls that test multiple parameters of a patient blood sample. The present teachings are directed to controls capable of testing multiple elements of a blood sample, which may include various white blood cell populations, nucleated red blood cells, reticulocytes or other blood cell types. In addition, the present teachings provide for one control product that produces consistent data for a number of hematology analyzers, as opposed to requiring a distinct control for each analyzer. As a further benefit of the present teachings, the preservation of the red blood cell membranes results in a shelf-stable product whereby the red blood cells resist hemoglobin leakage for a period of at least about 4 months, or longer. The leakage of hemoglobin from the red blood cells may render the control ineffective for its intended use, thus requiring that the red blood cell membranes be preserved to prevent this undesirable leakage.

By way of summary, the present invention meets some or all of the above needs by providing in a first aspect a composition comprising red blood cells in a suspension medium and one or more cis di-ahls; wherein more than 6 percent by weight of the hemoglobin in the red blood cells is S-A1c glycated. The one or more cis di-ahls comprise one or more compounds having two active hydrogen containing functional groups on adjacent carbon atoms. Preferably, the suspension medium is an aqueous suspension medium.

In another aspect, the present invention contemplates a method comprising contacting red blood cells in a suspension medium having a concentration of S-A1c glycated hemoglobin of greater than 6 percent by weight of the hemoglobin in the red blood cells with a sufficient amount of one or more cis di-ahls such that the concentration of S-A1c glycated hemoglobin in resulting composition as measured by high pressure liquid chromatography, immunoassay and boronate affinity methods is consistent.

In another aspect, the present invention contemplates a cellular hematology control for glycated hemoglobin contained in red blood comprising intact red blood cells having a predetermined level of greater than about 6 percent by weight of S-A1c glycated hemoglobin and one or more cis di-ahls in a stabilized suspension medium. The cellular hematology control for glycated hemoglobin contained in red blood may further comprise intact red blood cells having a predetermined level of less than about 6 percent by Weight of S-A1c glycated hemoglobin.

The invention may further comprise a cellular hematology control for glycated hemoglobin contained in red blood cells comprising a) red blood cells in a stabilized aqueous medium wherein the hemoglobin contains from about 4 to about 6 percent by weight of S-A1c glycated hemoglobin; b) red blood cells in a stabilized aqueous medium wherein the hemoglobin contains greater than about 6 and less about X percent by weight of S-A1c glycated hemoglobin based on the weight of the hemoglobin and one or more cis di-ahls; and c) red blood cells in a stabilized aqueous medium wherein the hemoglobin contains greater than about X to about 16 percent by weight of S-A1c glycated hemoglobin based on the weight of the hemoglobin and one or more cis di-ahls; wherein X is between about 7 and 14.

In a preferred embodiment, the cellular hematology control for glycated hemoglobin contained in red blood cells comprising a) red blood cells in a stabilized aqueous medium wherein the hemoglobin contains from about 4 to about 6 percent by weight of S-A1c glycated hemoglobin; b) red blood cells in a stabilized aqueous medium wherein the hemoglobin contains from about 7 to about 9 percent by weight of S-A1c glycated hemoglobin based on the weight of the hemoglobin and one or more cis di-ahls; and c) red blood cells in a stabilized aqueous medium wherein the hemoglobin contains from about 10 to about 14 percent by weight of S-A1c glycated hemoglobin based on the weight of the hemoglobin and one or more cis di-ahls.

In another preferred embodiment the cellular hematology control for glycated hemoglobin contained in red blood cells comprising a) red blood cells in a stabilized aqueous medium wherein the hemoglobin contains from about 4 to about 6 percent by weight of S-A1c glycated hemoglobin based on the weight of the hemoglobin; and b) red blood cells in a stabilized aqueous medium wherein the hemoglobin contains from about 10 to about 12 percent by weight of S-A1c glycated hemoglobin based on the weight of the hemoglobin and one or more cis di-ahls.

The invention further contemplates a method for determining the accuracy and reproducibility of the operation of an analytical instrument capable of measuring the glycated hemoglobin levels comprising a) providing a cellular hematology control of the invention in a known reference quantity: b) determining the glycated hemoglobin level in said control of a) with the instrument; and c) comparing the glycated hemoglobin levels obtained in b) with the known reference quantity.

In another aspect the invention is a composition comprising red blood cells having a portion of the hemoglobin as acetylated hemoglobin and a portion of hemoglobin as S-A1c glycated hemoglobin, wherein the red blood cells are glycated on the terminal valine amino acid of the Alpha or Beta chain, with the proviso that more than 6 percent by weight of the hemoglobin in the red blood cells are acetylated or glycated on the terminal valine amino acid of the Alpha or Beta chain. In yet another aspect, the present invention contemplates a method glycating and acetylating red blood cells comprising contacting red blood cells with glucose and acetylsalicylic acid in a suspension medium at about 35° C. to about 40° C. under conditions such that the resulting concentration of acetylated hemoglobin and S-A1c glycated hemoglobin is greater than about 6 percent by weight.

The novel compositions of the invention can be prepared from blood donors who are healthy, that is blood donors that do not have diabetes. The methods of preparing the controls can be performed in reasonable time frames that are acceptable in industrial environments and provide the flexibility to provide standards with varying levels of glycated S-A1c and exhibiting consistency among the standard test methods. The newly invented methods focused on the efficient manufacturing of blood samples with high A1c values from healthy blood samples with normal A1c values. These new methods were based on glycation of hemoglobin within intact red cells. These methods allow one to circumvent the difficulties associated with the processes described by Ryan et al, U.S. Pat. No. 7,361,513. In vitro glycation can produce blood samples with high A1c values using healthy blood sample with normal A1c values which are abundant and free of drugs or drug derivatives of hemoglobin. As these normal blood samples are obtained from healthy individuals, they are usually free from interfering abnormal hemoglobin variants. Additionally the in vitro glycation method also provides other advantages. The primary advantage is to have control on the manufacturing process to obtain any amount of high A1c level glycated blood sample to meet the increasing demand. The standardized glycation method also allows the manufacturer to eliminate lot to lot variation of A1c values or blood cell count. The other invented methods takes advantage of catalytic conditions to expedite the glycation of hemoglobin with glucose. Glycation of hemoglobin occurs in two steps. The first step is rapid condensation of glucose with hemoglobin producing a labile intermediated (L-A1c) followed by a slow rearrangement (Amadori rearrangement) reaction producing stable product, S-A1c. The key of this aspect of the invention is to accelerate the slow second step by heating or utilizing catalyst. The novelty of this glycation method is unprecedented application of a series of biocompatible purine based catalysts (e.g. inosine, adenosine) such that the slow in vitro glycation method can be used for manufacturing A1c controls in a reasonable time frame.

DETAILED DESCRIPTION

The invention generally relates to compositions useful in controls for testing hemoglobin for long term diabetic tendencies. Generally, the compositions comprise red blood cells having a portion of the hemoglobin as S-A1c glycated hemoglobin, wherein the red blood cells are glycated on the terminal valine amino acid of the Beta and/or the Alpha chain and one or more cis di-ahls, wherein more than 6 percent by weight of the hemoglobin in the red blood cells are glycated on the terminal valine amino acid of the Beta and/or Alpha chain. S-A1c glycated hemoglobin refers to stabilized hemoglobin wherein the terminal valine amino acid of the Beta and/or Alpha chain is bonded to the residue of a glucose or mannose molecule. S-A1c glycated hemoglobin is also known as S-A1c glycosylated hemoglobin. The term S-A1c glycated hemoglobin as used herein includes hemoglobin glycated with glucose and with mannose. Generally, the composition comprises red blood cells having a portion of the hemoglobin as acetylated hemoglobin and a portion of hemoglobin as S-A1c glycated hemoglobin, wherein the red blood cells are glycated on the terminal valine amino acid of the Alpha or Beta chain and acetylated, with the proviso that more than 6 percent by weight of the hemoglobin in the red blood cells are glycated on the terminal valine amino acid of the Alpha or Beta chain or acetylated. The process for the preparation of the S-A1c glycated hemoglobin using glucose involves a 2 step synthetic sequence as described in the equation.

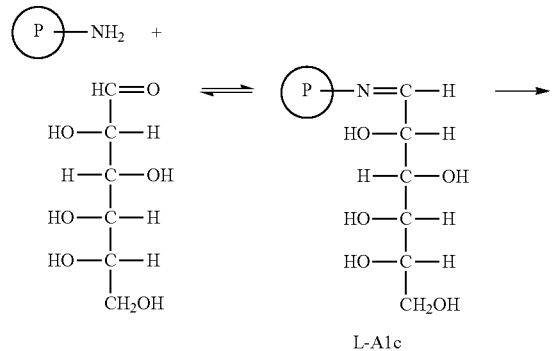

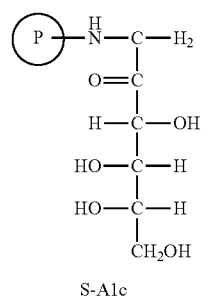

The process for the preparation of the S-A1c glycated hemoglobin using mannose involves a 2 step synthetic sequence as described in the equation.

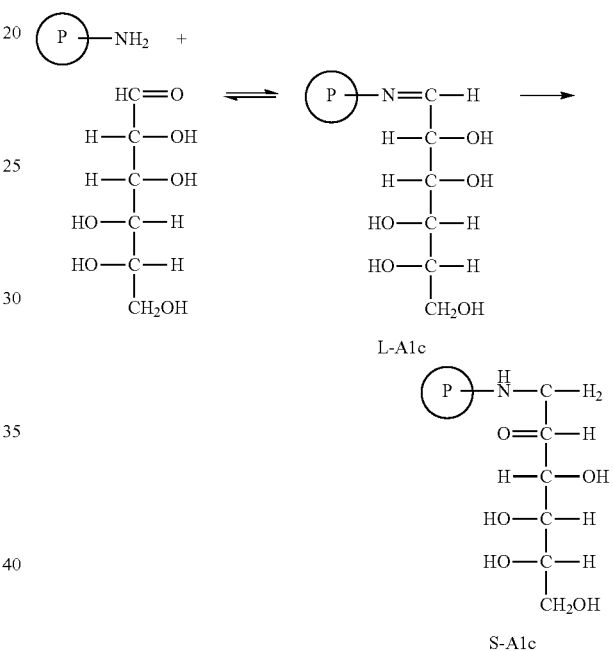

The first step is fast and reversible and yields a glycated intermediate which is a Shiff base. This first product is often referred to as labile glycated hemoglobin, L-A1c glycated hemoglobin. The second step is irreversible and a very slow step and is known as an Amadori rearrangement. The glycation may occur on the A1c binding site (Val 1 on the Beta Chain or Alpha Chain) and other non-A1c sites (other Lys residues). The composition of the invention can contain a range of concentration levels of S-A1c glycated hemoglobin in red blood cells. Any concentration level that is useful, for instance in blood control standards, may be utilized. Preferably, the concentration of S-A1c glycated hemoglobin in red blood cells is above 6 percent by weight, more preferably about 7 weight percent or greater and most preferably about 8 weight percent or greater. Preferably, the concentration of S-A1c glycated hemoglobin in red blood cells is about 16 weight percent or less, more preferably about 14 percent by weight or less and most preferably about 12 percent by weight or less. The normal range of concentration of S-A1c glycated hemoglobin in red blood cells found in normal blood donors is about 6 weight percent or below. Above 16 weight percent is above the range of S-A1c glycated hemoglobin in red blood, cells normally found in diabetic blood. The acetylation of hemoglobin is performed by reacting acetyl salicylic acid with hemoglobin. The acetylation occurs on one or more amine sites found in hemoglobin. The location of the acetylation is not entirely clear. Different reports in the literature have identified different sites for the acetylation. This reaction is illustrated by the following formula

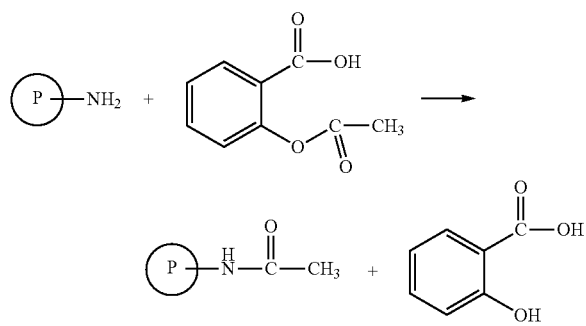

The composition of the invention can contain a range of concentration levels of acetylated hemoglobin and S-A1c glycated hemoglobin in red blood cells. Any concentration level that is useful, for instance in blood control standards, may be utilized. Preferably, the combined concentration of acetylated hemoglobin and S-A1c glycated hemoglobin in red blood cells is above 6 percent by weight, more preferably about 7 weight percent or greater and most preferably about 8 weight percent or greater. Preferably, the combined concentration of acetylated hemoglobin and S-A1c glycated hemoglobin in red blood cells is about 16 weight percent or less, more preferably about 14 percent by weight or less and most preferably about 12 percent by weight or less. The normal range of concentration of S-A1c glycated hemoglobin in red blood cells found in normal blood donors is about 6 weight percent or below. Above 16 weight percent is above the range of S-A1c glycated hemoglobin in red blood cells normally found in diabetic blood. The source of red blood cells is human blood. Preferably, the red blood cells are derived from the blood of a non-diabetic donor and more preferably a healthy donor. More preferably, the red blood cells used to synthesize the composition of the invention are stabilized red blood cells. Any stabilized red blood cells useful in manufacturing blood standards may be used to prepare the compositions of the invention. In a preferred embodiment, the stabilized red blood cells are stabilized as disclosed in Ryan et al U.S. Pat. No. 7,361,513 B2 as disclosed in Column 6 lines 37 to column 11, line 29, incorporated herein by reference. The novel compositions of the invention can be prepared from blood donors who are healthy, that is blood donors that do not have diabetes. The methods of preparing the controls can be performed in reasonable time frames that are acceptable in industrial environments and provide the flexibility to provide standards with varying levels of glycated S-A1c and exhibiting consistency among the standard test methods. The newly invented methods focused on the efficient manufacturing of blood samples with high A1c values from healthy blood samples with normal A1c values. These new methods were based on glycation of hemoglobin within intact red cells. These methods allow one to circumvent the difficulties associated with the processes described by Ryan et al, U.S. Pat. No. 7,361,513. In vitro glycation can produce blood samples with high A1c values using healthy blood sample with normal A1c values which are abundant and free of drugs or drug derivatives of hemoglobin. As these normal blood samples are obtained from healthy individuals, they are usually free from interfering abnormal hemoglobin variants. Additionally the in vitro glycation method also provides other advantages. The primary advantage is to have control on the manufacturing process to obtain any amount of high A1c level glycated blood sample to meet the increasing demand. The standardized glycation method also allows the manufacturer to eliminate lot to lot variation of A1c values or blood cell count. The other invented methods takes advantage of catalytic conditions to expedite the glycation of hemoglobin with glucose. Glycation of hemoglobin occurs in two steps. The first step is rapid condensation of glucose with hemoglobin producing a labile intermediated (L-A1c) followed by a slow rearrangement (Amadori rearrangement) reaction producing stable product, S-A1c. The key of this aspect of the invention is to accelerate the slow second step by heating or utilizing catalyst. The novelty of this glycation method is unprecedented application of a series of biocompatible purine based catalysts (e.g. inosine, adenosine) such that the slow in vitro glycation method can be used for manufacturing A1c controls in a reasonable time frame.

The glycated hemoglobin useful in this invention can be any glycated hemoglobin prepared utilizing glucose or mannose as glycating sugars. Among preferred processes for glycating hemoglobin are the processes disclosed herein and in Ryan et at U.S. Pat. No. 7,361,513 B2; and commonly owned application titled "METHOD OF PREPARING CONTROLS FOR GLYCATED HEMOGLOBIN S-A1c DERIVED FROM HEALTHY BLOOD CELLS" filed concurrently herewith on Nov. 17, 2011 claiming priority from, Ser. No. 61/416,623; all incorporated herein by reference.

In one embodiment, glycated hemoglobin is prepared by contacting the red blood cells and glucose in a reaction medium, optionally in the presence of a compound containing a purine ring having a ribose sugar ligand on the five membered ring of the purine compound under conditions that a portion of the hemoglobin is converted to S-A1c glycated hemoglobin, wherein the red blood cells are glycated on the terminal valine amino acid of the Beta chain and/or Alpha chain. In other words, as a result of this process the concentration of S-A1c glycated hemoglobin is increased, preferably to a level above 6 percent by weight of the hemoglobin present. In another embodiment the glycated hemoglobin is prepared by contacting red blood cells in a suspension medium containing mannose under conditions such that the concentration of S-A1c glycated hemoglobin is increased to greater than about 6 percent by weight of the hemoglobin in the red blood cells. Preferably the suspension medium is an aqueous suspension medium. In preferred embodiments, the method is performed at about ambient temperature, 18° C. to about 23° C.

In general terms, the process for preparing red blood cells containing S-A1c glycated hemoglobin comprises the following steps. In the first step, a portion of or all of the red blood cells are optionally contacted with an agent which prevents the hemoglobin in the red blood cells from converting from the iron II to iron III valence state. Thereafter, the red blood cells are washed with the reaction solution containing glucose or mannose to remove substantially all of the stabilizing solution in which the red blood cells were received. The red blood cells are then contacted with a reaction solution containing mannose, glucose or glucose and a purine ring containing compound having a ribose sugar based ligand on the five member ring under conditions such that a portion of the hemoglobin is converted to S-A1c glycated hemoglobin, wherein the red blood cells are glycated on the terminal valine amino acid of the Beta chain and/or Alpha chain. After the reaction mixture has reached the desired stage of glycated hemoglobin concentration, the red blood cells are washed with the reaction solution to remove unreacted mannose, glucose or glucose and purine derivative. At this stage the composition generally contains an elevated level of Labile Alc, the Schiff base described hereinbefore. Thus it is desirable to expose the red blood cells containing and S-Alc glycated hemoglobin and L-Alc hemoglobin to conditions to decompose the L-Alc hemoglobin to hemoglobin and glucose or mannose and to convert a relatively small portion of the L-Alc hemoglobin to S-Alc glycated hemoglobin. The relative ratio of L-Alc which decomposes to that which converts to S-Alc glycated hemoglobin is dependent upon the amount of glucose or mannose present in the reaction mixture. The formation of the L-Alc Schiff base is an equilibrium reaction. Preferably this step is performed in the absence of or at a low concentration of glucose or mannose such that most of the L-Alc Schiff base decomposes. Once the desired portion of L-Alc hemoglobin is decomposed and/or converted to S-Alc glycated hemoglobin, the red blood cells are placed into a fixing solution for a time sufficient to stabilize the red blood cells. Finally, the red blood cells are placed in a diluent containing one or more cis di-ahls and stored. Preferably the diluent in which the red blood cells are stored is a suspension medium. Preferably the suspension medium is suitable for delivering the resulting composition to an analytical instrument for analysis. The suspension medium contains a cis di-ahl in a sufficient amount such that the amount of S-Alc glycated hemoglobin reported by the boron affinity test is consistent with the amount reported by immunoassay and high pressure liquid chromatography.

In one aspect a composition of the invention is prepared by contacting the red blood cells with glucose and acetyl salicylic acid in a suspension medium under conditions that a portion of the hemoglobin is converted to acetylated hemoglobin and a portion of hemoglobin is converted to S-Alc glycated hemoglobin, wherein the red blood cells are glycated on the terminal valine amino acid of the Alpha or Beta chain. In general terms, the process for preparing red blood cells containing acetylated hemoglobin and S-Alc glycated hemoglobin comprises the following steps. In the first step, a portion of or all of the red blood cells are optionally contacted with an agent which prevents the hemoglobin in the red blood cells from converting from the iron II to iron III valence state. Thereafter, the red blood cells are washed with the reaction solution containing glucose to remove substantially all of the stabilizing solution in which the red blood cells were received. The red blood cells are then contacted with a reaction solution containing glucose and acetyl salicylic acid under conditions such that a portion of the hemoglobin is converted to acetylated hemoglobin and a portion of hemoglobin is converted to S-Alc glycated hemoglobin, wherein the red blood cells are glycated on the terminal valine amino acid of the Alpha or Beta chain. After the reaction mixture has reached the desired stage the red blood cells are washed with the reaction solution to remove unreacted glucose and acetyl salicylic acid. At this stage the composition generally contains an elevated level of Labile Alc, the Schiff base described hereinbefore. Thus it is desirable to expose the red blood cells containing acetylated hemoglobin and S-Alc glycated hemoglobin and L-Alc hemoglobin to conditions to decompose the L-Alc to hemoglobin and glucose and to convert a relatively small portion of the L-Alc hemoglobin to S-Alc glycated hemoglobin. The relative ratio of L-Alc which decomposes to that which converts to S-Alc glycated hemoglobin is dependent upon the amount of glucose present in the reaction mixture. The formation of the L-Alc Schiff base is an equilibrium reaction. Preferably this step is performed in the absence of or at a low concentration of glucose such that most of the L-Alc Schiff base decomposes. Once the desired portion of LAlc hemoglobin is decomposed and converted to S-Alc glycated hemoglobin, the red blood cells are placed into a fixing solution for a time sufficient to stabilize the red blood cells. Finally, the red blood cells are placed in a diluent and stored. Preferably the diluent in which the red blood cells are stored is a suspension medium. Preferably the suspension medium is suitable for delivering the resulting composition to an analytical instrument for analysis.

The stabilized red blood cells are typically received in a stabilized cell wash diluent. Any stabilized diluent utilized for carrying red blood cells may be used as the cell wash diluent. Preferred cell wash diluents used in the process of the invention are described in Ryan et al. U.S. Pat. No. 7,361,513 B2 at Column 7 line 44 to Column 8 line 17 as shown in Tables 1 and 2, incorporated herein by reference, and reproduced hereinafter. Certain Hb Alc preparations of the present invention utilize the cell wash diluent with the following general formulation, the solvent or carrier for these compositions is deionized water:

| Cell Wash Diluent Components | Concentration (% w/V) |
| --- | --- |
| Polyethylene Glycol (FW: 200-50,000) | 0-3% |
| EDTA (disodium) | 0-3% |
| Magnesium Gluconate ($C_{12}H_{22}MgO_{14} \cdot 2H_2O$) | 0-1% |
| Sodium Phosphate dibasic ($Na_2HPO_4$) | 0-2% |
| Glucose or Mannose | 0-8% |
| Methyl Paraben | 0-0.2% |
| Inosine | 0-0.5% |
| Neomycin Sulfate | |
| Chloramphenicol | |
| Sodium Hydroxide (NaOH) | |
| Potassium Chloride (KCl) | |
| Osmolality (mOsm) | |

The following is an example of the cell wash diluent that has been used to wash/stabilize red blood cell controls of the present invention.

| Cell Wash Diluent Components | Concentration (% w/V) |
| --- | --- |
| Polyethylene Glycol (FW: 20,000) | 0.70% |
| EDTA (disodium) | 0.70% |
| Magnesium Gluconate ($C_{12}H_{22}MgO_{14} \cdot 2H_2O$) | 0.39% |
| Sodium Phosphate dibasic ($Na_2HPO_4$) | 0.27% |
| Glucose or Mannose | 0 |
| Methyl Paraben | 0.04% |
| Inosine | 0.025% |
| Neomycin Sulfate | 0.04% |
| Chloramphenicol | 0.015% |
| Sodium Hydroxide (NaOH) | 0.08% |
| Potassium Chloride (KCl) | 0.632% |
| pH (Final) | 7.0 |
| Osmolality (mOsm) | 300 |

Prior to the glycation step, or acetylation and glycation step, a portion of or all of the red blood cells are optionally contacted with an agent which prevents the hemoglobin in the red blood cells from converting from the iron II to iron III valence state. Hemoglobin has Fe (iron) II at the center which is utilized to bind and carry oxygen in the blood stream. When the Fe at the center of the hemoglobin is in the II ionic state the red blood cells retain a red color. The Fe II can undergo oxidation to form Fe III which causes the red blood cells to turn brown. Thus it is desirable to prevent the oxidation of the Fe II sites to Fe III. This is achieved by contacting the red blood cells with an agent that prevents oxidation of the Fe in the center of the hemoglobin. Any such agent which prevents this oxidation may be utilized. It is believed that the antioxidation agent bonds to the Fe at the center of the hemoglobin which prevents the Fe from oxidizing. Examples of such agents include carbon monoxide (CO) and the like. A preferred anti oxidation agent is carbon monoxide. The antioxidation agent is preferably contacted with the red blood cells while the red blood cells are located in a cell wash diluent, preferably in a stabilized a cell wash diluent. Where the antioxidation agent is a gas, such as carbon monoxide, the gaseous antioxidation agent is bubbled through the cell wash diluent containing the red blood cells. Where the antioxidation agent is a liquid or solid it is mixed into the cell wash diluents. The antioxidation agent is contacted with the red blood cells under conditions such that a sufficient number of the Fe II cites at the center of the hemoglobin in the red blood cells are bonded to or associated with antioxidants such that the red blood cells retain a red color. Preferably about 40 mole percent or greater of the Fe II sites are bonded to or associated with an antioxidant, more preferably about 45 mole percent or greater and most preferably about 49 mole percent or greater. Preferably about 60 mole percent or less of the Fe II sites are bonded to or associated with an antioxidant, more preferably about 55 mole percent or less and most preferably about 51 mole percent or less. If too many of the Fe II sites in the hemoglobin of the red blood cells are bonded to or associated with antioxidant molecules, untreated red blood cells in cell wash diluents can be added to the treated red blood cells to provide the desired concentration of antioxidant modified hemoglobin. In the preferred embodiment wherein the antioxidant is carbon monoxide, the carbon monoxide is bubbled through the cell wash diluent containing the red blood cells until the amount of the Fe II sites of the hemoglobin are bonded to or associated with antioxidant molecules of the red blood cells is greater than desired. Thereafter, a portion of untreated red blood cells in cell wash diluent are added to the treated red blood cells to provide the desired concentration of antioxidant treated hemoglobin in the red blood cells.

The red blood cells are separated from the stabilized cell wash diluent. The separation is performed using any known method of separating solid materials from liquid media, provided the cells are not damaged. Examples of preferred separation techniques include filtration, centrifuging the medium with blood cells contained therein, dialysis and the like. Preferably, the contacting is performed as a series of washes wherein the red blood cells are separated from the wash solution by means known in the art, for example filtration or centrifugation. Thereafter, the red blood cells are then contacted with the medium used for the glycation reaction.

A cell wash diluent may be utilized as the reaction medium, included in the reaction media useful are those disclosed in Table 4 of Ryan et al. U.S. Pat. No. 7,361,513 B2 at Column 9, lines 24 to 45 which is reproduced as Table 3 hereinafter. Preferably, the reaction medium is aqueous based and acts as a suspension medium for the red blood cells. In this embodiment, the reaction medium can also be referred to as a suspension medium. The reaction medium is based on deionized water.

TABLE 3

| Reaction Medium Components | Concentration (% w/V) |
|---|---|
| Polyethylene Glycol (FW: 200-50,000) | 0-3% |
| EDTA (disodium) | 0-3% |
| Magnesium Gluconate ($C_{12}H_{22}MgO_{14} \cdot 2H_2O$) | 0-1% |
| Sodium Phosphate dibasic ($Na_2HPO_4$) | 0-2% |
| Glucose or Mannose | 0-8% |
| Methyl Paraben | 0-0.2% |

TABLE 3-continued

| Reaction Medium Components | Concentration (% w/V) |
|---|---|
| Inosine | 0-0.6% |
| Neomycin Sulfate | 0-0.2% |
| Chloraphenicol | 0-0.2% |
| Potassium Chloride (KCl) | 0-1.5 |
| Sodium Fluoride (NaF) | 0-0.5% |
| Ciprofloxacin* | 0-0.1% |
| Sodium Hydroxide (NaOH) | 0-0.5% |
| pH (final) | 6.0-8.0 |
| Osmolality (mOsm) | 250-350 |

*Final Addition.

The composition in Table 3 may also used in the stabilizing media of the final composition of the invention, and the ingredients marked final addition are added after completion of the glycation. The reaction medium further contains bovine serum albumin, which is present for the purpose of anticoagulation and anti-hemolysis. A sufficient amount of bovine serum albumin is present in the reaction medium to prevent the coagulation of the cells and hemolysis of the cells. The lower limit on the concentration of bovine serum albumin in the reaction medium is lowest concentration at which hemolysis or coagulation are prevented. Preferably, bovine serum albumin is present in the reaction medium in a concentration of about 1 percent by weight or greater and more preferably about 3 percent by weight or greater. The upper limit on the concentration of bovine serum albumin in the reaction medium is that concentration at which no further reduction of coagulation and hemolysis is possible. Preferably, bovine serum albumin is present in the reaction medium in a concentration of about 10 percent by weight or less, more preferably about 5 percent by weight or less and most preferably about 4 percent by weight or less. The reaction medium further contains glucose or mannose in sufficient amount to glycate, or glycated and acetylate the hemoglobin to the desired level. The lower limit on the concentration of glucose or mannose in the reaction medium is that concentration at which hemoglobin is glycated at a reasonable rate. Preferably, glucose is present in the reaction medium in a concentration of about 3 percent by weight or greater and more preferably about 5 percent by weight or greater. The upper limit on the concentration of glucose in the reaction medium is about 10 percent. Preferably, glucose is present in the reaction medium in a concentration of about 8 percent by weight or less, more preferably about 7 percent by weight or less and most preferably about 6 percent by weight of less. When Mannose is the glycating agent, the reaction medium further contains mannose in sufficient amount to glycate the hemoglobin to the desired level. The lower limit on the concentration of mannose in the reaction medium is that concentration at which hemoglobin is glycated at a reasonable rate. Preferably, mannose is present in the reaction medium in a concentration of about 4 percent by weight or greater and more preferably about 5 percent by weight or greater. The upper limit on the concentration of mannose in the reaction medium is about 8 percent and most preferably about 6 percent by weight of less. The reaction medium may further contains acetyl salicylic acid in sufficient amount to acetylate the hemoglobin to the desired level. The lower limit on the concentration of acetyl salicylic acid in the reaction medium is that concentration at which hemoglobin is acetylated at a reasonable rate. Preferably, acetyl salicylic acid is present in the reaction medium in a concentration of about 0.1 percent by weight or greater, more preferably about 0.2 percent by weight or greater and most preferably about 0.24 percent by weight or greater. The upper limit on the concentration of acetyl salicylic acid in the reaction medium is the solubility of the acetyl salicylic acid in the reaction medium. Preferably, acetyl salicylic acid is present in the reaction medium in a concentration of about 0.4 percent by weight or less, more preferably about 0.3 percent by weight or less and most preferably about 0.26 percent by weight of less. The concentration of red blood cells in the reaction medium is chosen such that the hemoglobin contained therein can be glycated and acetylated at a reasonable rate. If the concentration is too high the reaction rate is too slow. The concentration of red blood cells in the reaction medium is chosen such that the hemoglobin contained therein can be glycated at a reasonable rate. If the concentration is too high the reaction rate is too slow.

In one embodiment, the red blood cells are contacted with glucose in the presence of a purine compound having a ribose ligand bonded to the five membered ring of the purine compound. Any purine compound having a ribose sugar ligand bonded to the five membered ring of the purine compound that catalyzes the reaction of glucose with hemoglobin to form SA1c glycated hemoglobin may be utilized in this step. In a preferred embodiment the ribose ligand is bonded to a nitrogen atom on the five membered ring of the purine compound. The purine compound may contain one or more substituents on one or more of the purine rings. Any substituents that do not interfere with catalyzing the reaction of glucose with hemoglobin may be present on the purine ring. Preferably such substituents are capable of hydrogen bonding with groups on the hemoglobin molecule. Preferably such substituents are capable of hydrogen group abstraction. The substituents are preferably are selected from the group of amines, hydroxyls, thiols, amides, carboxylic acids, carboxylic amides, and oxygen doubly bonded to a carbon on one of the rings. Preferably such substituents are selected from the group of primary amines and oxygen doubly bonded to a carbon on one of the rings. Preferably the substituents are located on the six membered ring. The ribose sugar ligand can have one or mores substituents bonded thereto. Preferably two or more of the carbons on the ribose sugar ring have hydroxyl groups or oxygen atoms bonded thereto and most preferably hydroxyl groups. The ribose sugar ligand may have bonded to one or more oxygen atoms a phosphate group. In a preferred embodiment the purine compound corresponds to the formula

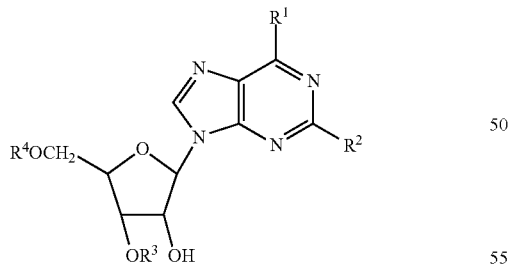

wherein $R^1$, $R^2$, $R^3$ and $R^4$ are separately in each occurrence hydrogen or a substituent that does not interfere with the reaction of glucose with hemoglobin. Preferably, $R^1$ and $R^2$ are separately in each occurrence hydrogen or functional groups which are capable of hydrogen bonding to parts of hemoglobin. More preferably, $R^1$ and $R^2$ are separately in each occurrence hydrogen or selected from the group of amines, hydroxyls, thiols, amides, carboxylic acids, carboxylic amides, and oxygen doubly bonded to a carbon on the six membered ring. Even more preferably, $R^1$ and $R^2$ are separately in each occurrence hydrogen or selected from the group of primary amines and oxygen doubly bonded to a carbon on the six membered ring. Preferably, $R^3$ is separately in each occurrence hydrogen or a phosphate group (the phosphorous of the phosphate group is bonded to oxygen) and most preferably hydrogen. Included among preferred purine containing compounds are inosine, adenosine, guanosine, xanthosine, 2-aminoadenosine, AMP (Adenosine monophosphate) and Cyclic AMP. Even more preferred purine containing compounds are inosine and adenosine. The preferred compounds correspond to the following formulas:

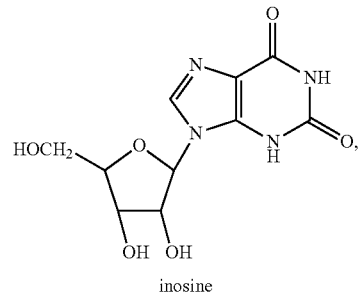
inosine

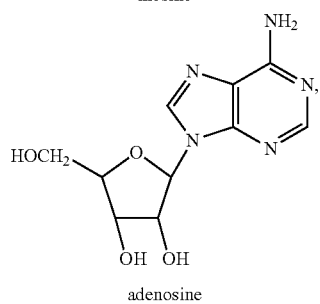
adenosine

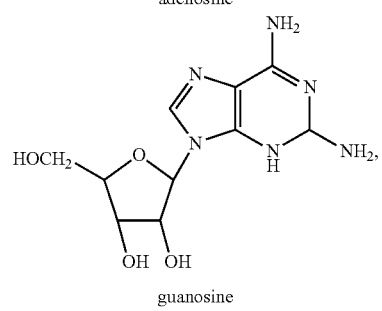
guanosine

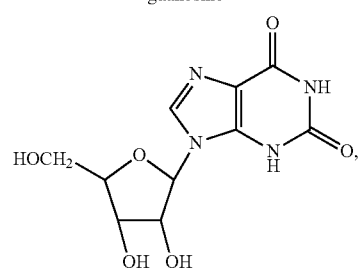
xanthosine

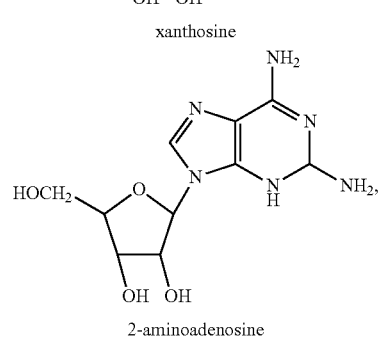
2-aminoadenosine

-continued

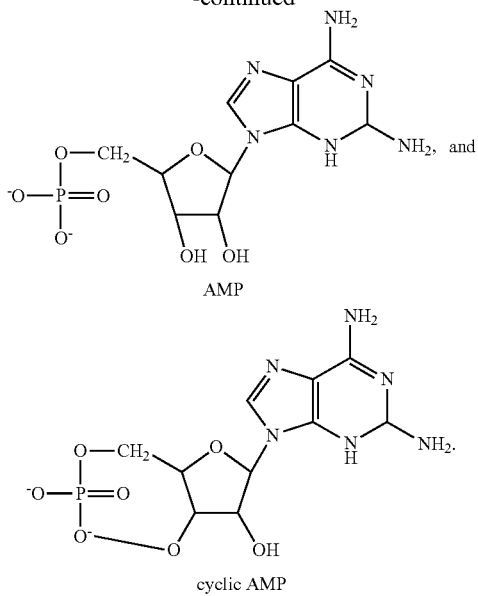

AMP cyclic AMP

The purine compounds are utilized in the step of contacting red blood cells with glucose in a sufficient amount to catalyze the glycation of hemoglobin. Preferably the purine compounds are present in an amount of about 0.1 percent by weight or greater based on the weight of the reaction medium, such as an aqueous suspension medium, and more preferably about 0.2 percent by weight or greater. Preferably, the purine compounds are present in an amount of about 0.5 percent by weight or less based on the weight of the reaction medium, such as an aqueous suspension medium, and more preferably about 0.4 percent by weight or less.

In a preferred embodiment, the concentration of red blood cells is the same concentration as found in human blood. It is preferred to monitor the concentration of hemoglobin in the reaction medium. Preferably the concentration of hemoglobin in the reaction medium is about 9 grams per deciliter (g/dL) or greater and more preferably about 10 grams per deciliter (g/dL) or greater. Preferably the concentration of hemoglobin in the reaction medium is about 12 grams per deciliter (g/dL) or less and more preferably about 11 grams per deciliter (g/dL) or less. The concentration can also be expressed as the concentration of red blood cells which is preferably about 4.0 million red blood cells per microliter of reaction medium or greater and more preferably about 5.0 millions red blood cells or greater. Preferably the concentration of red blood cells in the reaction medium is 7.0 million of red blood cells per microliter of reaction medium or less.

In the embodiment wherein glucose is the glycating agent, and where acetyl salicylic acid is optionally present, the reaction medium is exposed to elevated temperatures for sufficient time to achieve the desired concentration of S-A1c glycated hemoglobin. The temperature is chosen such that the glycation reaction proceeds at a reasonable rate and not so high that the red blood cells are damaged. Preferably, the reaction is performed at a temperature of about 35° C. or greater and more preferably at a temperature of about 37° C. or greater. Preferably, the reaction is performed at a temperature of about 40° C. or less and more preferably at a temperature of about 38° C. or less. Where mannose is the glycating agent these temperatures may be utilized although it is preferred to glycate with mannose at lower temperatures down to room temperature.

In the embodiment wherein mannose is the glycating agent, the reaction medium is exposed to temperatures for at which the desired concentration of S-A1c glycated hemoglobin can be reached in a reasonable time period. The temperature is chosen such that the glycation reaction proceeds at a reasonable rate and not so high that the red blood cells are damaged. Preferably, the reaction is performed at a temperature of about 18° C. or greater and more preferably at a temperature of about 23° C. or greater. Preferably, the reaction is performed at a temperature of about 40° C. or less, and more preferably at a temperature of about 38° C. or less, even more preferably at a temperature of about 25° C. or less and more preferably at a temperature of about 23° C. or less.

Generally, the glycation reaction is performed for a time sufficient to achieve the desired concentration of S-A1c glycated hemoglobin. In a preferred embodiment, the process of the reaction is monitored by an analytical technique which measures the concentration of the S-A1c glycated hemoglobin in the reaction medium. Any analytical technique which measures the concentration of S-A1c glycated hemoglobin can be used. Among preferred analytical techniques is high pressure liquid chromatography (HPLC). In a preferred embodiment, the high pressure liquid chromatography is performed utilizing an A1c 2.2 Plus or G8 Analyzer available from TOSOH Bioscience. Preferably the reaction is allowed to proceed until the concentration of S-A1c glycated hemoglobin, or S-A1c glycated hemoglobin and acetylated hemoglobin, in the red blood cells is greater than about 6 percent by weight based on the concentration of hemoglobin in the red blood cells and more preferably about 7 or greater. Preferably, the reaction is allowed to proceed until the concentration of S-A1c glycated hemoglobin, or S-A1c glycated hemoglobin and acetylated hemoglobin, in the red blood cells is about 16 percent by weight or less based on the concentration of hemoglobin in the red blood cells and more preferably about 14 percent by weight or less.

Where glucose alone is the glycating agent the reaction time is defined in Ryan et al. U.S. Pat. No. 7,361,513 B2. Wherein glucose in the presence of a purine compound, or acetyl salicylic acid, is the glycating agent or Mannose is the glycating agent and elevated temperatures are used, the reaction is performed for a time period such that the desired concentration of S-A1c glycated hemoglobin in the red blood cells is reached. Preferably, the reaction time is 20 hours or greater and more preferably 22 hours or greater. Preferably the reaction time is 30 hours or less and more preferably 24 hours of less. The reaction time is dependent on the reaction temperature and the mannose or glucose and purine compound or acetyl salicylic acid concentrations. At lower temperatures the reaction times are longer and at higher temperatures the reaction time is shorter. For this reason it is important to monitor the concentration of S-A1c glycated hemoglobin in the reaction mixture.

Where mannose is the glycating agent and the glycation occurs at about room temperature, the reaction is performed for a time period such that the desired concentration of S-A1c glycated hemoglobin in the red blood cells is reached. Preferably, the reaction time is 4 days or greater and more preferably 6 days or greater. Preferably the reaction time is 8 days or less. The reaction time is dependent on the reaction temperature and the mannose concentration. At lower temperatures the reaction times are longer and at higher temperatures the reaction time is shorter. For this reason it is important to monitor the concentration of S-A1c glycated hemoglobin in the reaction mixture.

The reaction can be performed in the presence of air and can be performed in either an open or closed vessel. A closed vessel is preferred as it provides for greater control of the reaction environment.

Once the desired concentration is achieved the reaction medium is allowed to cool, preferably to room temperature, about 18° C. to about 25° C., and preferably about 22° C. Thereafter, the glucose, optional acetyl salicylic acid, or mannose is removed from the reaction mixture to prevent further glycation. Any method of removing the glucose, optional acetyl salicylic acid, or mannose known to the skilled artisan may be utilized. Preferably, the red blood cells are removed from the reaction medium by a known separation technique, such as filtration, centrifuging or dialysis. The red blood cells are preferably washed with a diluent. Preferably the diluent utilized is a diluent as described in Table 3. In order to insure that all of the glucose or mannose is removed from the red blood cells, it is preferred to wash the red blood cells multiple times with the diluents. The red blood cells are washed with the diluent a sufficient number of times to remove substantially all of the glucose or mannose from the red blood cells. Generally, three washes results in a sufficient removal of the glucose or mannose. In a preferred embodiment the diluent contains bovine serum albumin, preferably in a concentration of about 3 percent to about 5 percent.

The red blood cells recovered from the glycation process generally contain a higher concentration of minor by-products, such as L-A1c hemoglobin, than typically found in diabetic blood. Thus it is preferable to adjust the level of the minor by-products in the blood by a deglycation step. In this step the red blood cells are dispersed in a diluent. Any diluent known to one skilled in the art may be used. Generally any diluent utilized for the first step may be used with the exception that mannose, glucose or glucose and purine compounds are not present. During the deglycation process the red blood cells dispersed in a diluent are exposed to an elevated temperature for a period of time such that the concentration of minor byproducts is adjusted to be in the normal range. Normal range, as used in this context, means the concentration of the minor byproducts are within the range minor byproducts that are found in naturally occurring red blood cells having the same concentration of S-A1c glycated hemoglobin. Any temperature which allows the conversion of the minor byproducts to an acceptable range in a reasonable time frame and which does not harm the red blood cells may be utilized. If the temperature is too low the reaction time is too long. If the temperature is too high the red blood cells can be damaged, such as through hemolysis. In the embodiment wherein glucose is the glycating agent, the deglycation is preferably performed at ambient (room temperature) or above and more preferably at a temperature of about 25° C. or greater and more preferably at a temperature of about 30° C. or greater. Preferably, the deglycation is performed at a temperature of about 40° C. or less and more preferably at a temperature of about 38° C. or less. Where the glycation agent is mannose, the deglycation is performed preferably at ambient (room temperature) 18° C. or above. Preferably, the deglycation is performed at a temperature of about 40° C. or less, and more preferably at a temperature of about 38° C. or less, even more preferably about 30° C. or less, even more preferably about 25° C. or less and most preferably about 23° C. or less. The deglycation time period is chosen to achieve the desired concentration of minor by-products. In a preferred embodiment, the concentration of L-A1c glycated hemoglobin is used to determine if the concentration of minor by-products is in an acceptable range. The L-A1c glycated hemoglobin is generally dissociated in this step. In a preferred embodiment, the deglycation process is monitored by an analytical technique which measures the concentration of the L-A1c glycated hemoglobin in the reaction medium. Any analytical technique which measures the concentration of L-A1c glycated hemoglobin can be used. Among preferred analytical techniques useful is high pressure liquid chromatography as described herein before. Preferably, the deglycation is performed under conditions such that the resulting concentration of L-A1c glycated hemoglobin is about 4 percent by weight or greater and most preferably about 4.2 percent by weight or greater. Preferably, the deglycation is performed under conditions such that the resulting concentration of L-A1c glycated hemoglobin is about 5 percent by weight or less and most preferably about 4.8 percent by weight or less.

The deglycation time is chosen such that the desired concentration of L-A1c is achieved. Preferably, the deglycation time is about 20 hours or greater and more preferably about 22 hours or greater. Preferably the deglycation time is about 30 hours or less and more preferably about 24 hours of less. The deglycation time is dependent on the reaction temperature. At lower temperatures the reaction times are longer and at higher temperatures the reaction time is shorter. For this reason it is important to monitor the concentration of L-A1c hemoglobin in the reaction mixture. The deglycation can be performed in the presence of air and can be performed in either an open or closed vessel. A closed vessel is preferred as it provides for greater control of the deglycation environment.

Once the desired concentration of L-A1c glycated hemoglobin is achieved the reaction medium is allowed to cool, if necessary, preferably to room temperature, about 22° C. Preferably, the red blood cells are removed from the reaction medium by a known separation technique, such as filtration and/or centrifugation. The red blood cells are preferably washed with a diluent. Preferably the diluent utilized is a diluent as described in Table 3. It is preferred to wash the red blood cells multiple times with the diluent. The red blood cells are washed with the diluent a sufficient number of times to remove substantially all of the unwanted by-products. Generally three washes result in a sufficient removal of the unwanted by-products. Preferably the stabilizing diluent is water based, aqueous, and the stabilizing diluent suspends the red blood cells, that is the final composition is located in an aqueous suspension medium.

Thereafter, the red blood cells are contacted with a fixing solution as disclosed in Ryan et. al. U.S. Pat. No. 7,361,513 at Column 8 lines 19 to 44, incorporated herein by reference. The red blood cells are fixed using a known cell fixing compound or composition. The cell fixing compound or composition serves to strengthen the cell membrane and to minimize the change in mean cell volume (MCV), thus to prevent the hemolysis of red blood cells. In addition, the fixation allows the cell fixing compound or composition to cross link hemoglobin, which creates more homogeneity and stability of chemical charge for hemoglobin and enhances its HPLC performance during long-term stability testing. The fixative may include, but is not limited to, one or more of an aldehyde, oxazolidine, alcohol, cyclic urea, or the like. Examples of such fixatives include, without limitation, formaldehyde, glutaraldehyde, diazolidinyl urea (DU), imidazolidinyl urea (IDU), dimethylol urea, dimethylol-5,5-dimethylhydantoin, 2-bromo-2-nitropropane-1,3-diol; quaternary adamantine, hydroxyl-methyl-1-aza-3,7-dioxabicyclo (3.3.0)octane, sodium hydroxymethyl glycinate, and mixtures thereof, or the like. Other fixatives may be used such as those disclosed in U.S. Pat. Nos. 5,196,182; 5,262,327; 5,460,797; 5,811,099; 5,849,517; 6,221,668; 5,529,933; 6,187,590 (incorporated herein by reference). The appropriate fixative reagent is selected based upon the cell attribute to be evaluated by a hematology analyzer. In a preferred embodiment, the present invention utilizes a fixation process to generate the control composition. In one particular embodiment of the present invention, the blood cell fixation begins by contacting the washed blood cells with a fixative reagent. A more preferred cell fixation compound is glutaraldehyde. A cell fixation procedure using glutaraldehyde is performed between cell filtration and cell final wash. A general cell fixation procedure includes the following steps: adjusting the count of filtered RBC to approximately 4±0.2 M/µL, using the cell wash diluent described in Table 2; measure the total volume of RBC; measuring the same volume of cell wash diluent in another container. Add 0.1-4.0 mL/L of glutaraldehyde (25 percent stock) to the diluent and mixing well; mixing the RBC solution and glutaraldehyde solution thoroughly; and place the mixed solution at room temperature for 24 hours before final cell washing. An example of the cell fixation procedure included the preparations of a 4.0 M/µL RBC solution and a 0.8 mL/L glutaraldehyde solution and a quick mixing of the two solutions at room temperature.

After the cell fixation is complete, the red blood cells are separated from the fixation compound or composition using known separation techniques, such as filtration, centrifuging, dialysis or a combination thereof. Thereafter, red blood cells are washed using a cell wash diluent such as a composition as described in table 3. Multiple washes are generally utilized. After every wash the red blood cells are separated from the cell wash diluent.

After washing, the red blood cells are suspended in a final stabilizing medium (diluent). The final stabilizing diluent is used to stabilize the various controls of the present invention. The final stabilizing diluent is preferably an aqueous based medium. It is desirable for the final stabilizing diluent to possess the following attributes: (1) to stabilize the value of, percentage of S-A1c glycated hemoglobin at both closed-vial and open-vial modes; and (2) to prevent red blood cell hemolysis. Similar to the cell wash diluent, the final stabilizing diluent includes appropriate cell stabilizers (e.g. magnesium gluconate, EDTA and PEG), cell metabolites (e.g. inosine and glucose), buffers (e.g. sodium phosphate dibasic and/or monobasic), antibiotics/antimicrobial agents (e.g. neomycin sulfate and chloramphenicol), and anti-fungal agents (e.g. methyl paraben). In addition, final stabilizing diluent contains one or more of the following components: glucose, and sodium. The formulations of final stabilizing diluents vary slightly depending upon the desired level of S-A1c hemoglobin in the different levels of S-A1c hemoglobin controls (such as Level I or II). The final stabilizing diluent does not have to contain all of the components listed in Table 3, but will include at least as many of the components listed in Table 3 to provide the desired, S-A1c hemoglobin levels. In one preferred embodiment the suspension medium contains from about 0.3 to about 0.6 percent by weight of glucose based on the weight of the suspension medium.

The stabilized suspension of red blood cells may contain one or more cis di-ahls. A cis di-ahl is a compound having two ahl groups on adjacent carbon atoms. An ahl group is a functional group containing an active hydrogen atom. Thus a cis di-ahl is a compound having functional groups containing active hydrogen atoms on adjacent carbon atoms. Functional groups having active hydrogen atoms are well known to those skilled in the art. Preferred functional groups containing active hydrogen atoms include hydroxyl, amino, thiol and carboxylate functional groups; with amino, thiol and hydroxyl being more preferred and hydroxyl most preferred. Any cis di-ahl can be used herein that binds to the resin used in the boronate affinity analytical method and which does not alter the results of the other analytical test used for measuring the S-A1c levels in red blood cell hemoglobin. Preferably the one or more cis di-ahls are cell impermeable so that they do not swell or increase the cell volume of the red blood cells. Preferably the one or more cis di-ahls do not react with mannose, glucose or functional groups on hemoglobin. Preferred classes of di-ahls include cis diols, cis diamines, cis dicarboxylic acids, cis thiols, compounds with cis amino and hydroxyls, compounds with cis thiol and hydroxyl groups, and compounds with cis amino and thiol groups. More preferred classes of cis di-ahls are cis-diols. Preferred cis di-ahls include sugars (fructose), reduced sugars (sorbitol, manitol, xylitol), serine, cysteine and dithiothreitol. More preferred cis di-ahls include sorbitol, fructose and manitol with sorbitol most preferred. The cis di-ahls are added to the stabilized suspension medium (diluent) as described hereinbefore. The amount of cis di-ahl used is selected such that the amount of S-A1c glycated hemoglobin reported by the boron affinity test is consistent with the amount reported by immunoassay and high pressure liquid chromatography. Consistent as used in this context means the reported percentage of S-A1c glycated hemoglobin reported by the boron affinity test is no more than 2 percentage points different than reported by immunoassay and high pressure liquid chromatography, and more preferably no more than 1 percentage point. The amount of cis di-ahl in the stabilized diluent, preferably an aqueous suspension medium, is about 1.0 percent by weight or greater based on the weight of the stabilized diluent, more preferably about 2.0 percent by weight or greater and most preferably about 3.0 percent by weight or greater. The amount of cis di-ahl in the stabilized diluent, preferably an aqueous suspension medium, is about 10.0 percent by weight or less based on the weight of the stabilized diluent, more preferably about 8.0 percent by weight or less and most preferably about 6.0 percent by weight or less.

As discussed herein there are several washing steps. Typically, washing will employ contacting the cells with a suitable solution, preferably a buffered solution, and most preferably a suitable isotonic wash solution. The wash solution, which generally will be substantially isotonic, may include any of a number of ingredients in a deionized and/or distilled water base. For example, the wash solution may include at least one or more, more preferably two or more, still more preferably three or more, still more preferably four or more and still even more preferably all of the following ingredients: a fungicide; an antimicrobial; a surfactant; a buffer; a metal chelating agent; a cell nutrient; or an agent for maintaining tonicity. For example, in one particular embodiment of the present invention, the relative amounts of the above ingredients may be as follows: a fungicide of up to about 5 parts; an antimicrobial of up to about 5 parts; a surfactant ranging from about 5 parts to about 20 parts; a buffer ranging from about 5 parts to about 30 parts, a metal chelating agent ranging from about 25 parts to about 50 parts; a cell nutrient of up to about 5 parts; and an agent for maintaining tonicity in about 15 parts to about 35 parts. The wash solution may also contain other ingredients as described in U.S. Pat. No. 5,858,790 or U.S. Pat. No. 6,187,590 (incorporated by reference herein). The isotonic wash solution may also include ingredients that act as a homolysis inhibitor, an aggregating agent, a cell stabilizer, an antioxidant, or a mixture thereof. By way of example, one possible wash solution may include about 40 mg percent Methyl Paraben, about 300 mg percent polyethylene glycol (PEG)—(molecular weight about 20,000); about 1675 mg percent ethylenediaminetetraacetic acid (EDTA); about 933 mg percent magnesium gluconate; about 639 mg percent sodium phosphate dibasic anhydrous, about 25 mg percent adenosine, about 25 mg percent Inosine; about 40 mg percent neomycin sulfate; and about 15 mg percent chloramphenicol.

The fixation may take place at any temperature and preferably at room temperature, about 18° C. to 25° C. in a preferred embodiment of the present invention, the fixed red blood cells are washed out of the fixative reagent and re-suspended into a suitable suspension medium. The cells can be washed out of the fixative reagent with a buffered isotonic solution. In one preferred embodiment, after contact with the hypotonic solution, the cells are re-suspended in a diluent. In one preferred embodiment, the cells are resuspended, for instance, in a phosphate buffered solution containing polyethylene glycol 20,000 (PEG), ethylenediamine tetraacetic acid (EDTA) and magnesium gluconate with 2 percent bovine serum albumin.

The red blood cells processed as described herein before can be utilized to prepare controls used to calibrate instruments used to measure the level of certain components in blood. The red blood cells prepared as described herein are preferably used to calibrate instruments that measure the level of S-A1c glycated hemoglobin or S-A1c glycated hemoglobin and acetylated hemoglobin. Preferably controls containing the red blood cells of the invention are used to calibrate apparatus which analyze red blood cells by high pressure liquid chromatography, immunoassay and boronate affinity. In a preferred embodiment, the concentration of S-A1c glycated hemoglobin, or S-A1c glycated hemoglobin and acetylated hemoglobin, in the red blood cell controls of the invention as measured by high pressure liquid chromatography, immunoassay and boronate affinity methods are consistent, more preferably the measured concentration of S-A1c glycated hemoglobin, or S-A1c glycated hemoglobin and acetylated hemoglobin, in the red blood cell controls of the invention as measured by high pressure liquid chromatography, immunoassay and boronate affinity methods are within a range of about 2 percent by weight or less of each other and more preferably about 1 percent by weight or less.

The controls of the invention comprise the red blood cells of the invention in an appropriate suspension medium. The controls are used for cellular hematology controls. The suspension medium can be any suspension medium utilized for red blood cell controls. The suspension medium can comprise the compositions described hereinbefore as the final stabilizing medium. The suspension media are preferably water based. The controls contain one or more sets of red blood cells in a suspension medium having a known concentration of S-A1c glycated hemoglobin and one or more cis di-ahls. Preferably, the controls contain two or more sets of red blood cells in a suspension medium having a known concentration of S-A1c glycated hemoglobin, or S-A1c glycated hemoglobin and acetylated hemoglobin, and one or more cis di-ahls. In a more preferred embodiment, the controls comprise two or three sets of red blood cells in a suspension medium having a known concentration of S-A1c glycated hemoglobin and one or more cis di-ahls. A combination of two or more sets of red blood cells can be assembled into kits. Preferably, the controls contain one set of red blood cells with S-A1c glycated hemoglobin in the normal range, non-diabetic range, of about 4 to 6 percent by weight. Preferably, the controls contain one or more sets of red blood cells having concentrations of S-A1c glycated hemoglobin, or S-A1c glycated hemoglobin and acetylated hemoglobin, of greater than about 6 percent by weight, more preferably about 7 percent by weight or greater and most preferably about 8 percent by weight or greater. Preferably, the controls contain one or more sets of red blood cells having concentrations of S-A1c glycated hemoglobin, or S-A1c glycated hemoglobin and acetylated hemoglobin, of about 16 percent by weight or less, more preferably about 14 percent by weight or less and most preferably about 12 percent by weight or less. The sets of the controls having greater than about 6 percent by weight of glycated hemoglobin contain one or more cis di-ahls. The controls which contain S-A1c glycated hemoglobin in the normal range, 6 percent or less, do not require the presence of a cis di-ahl.

The controls of the invention contain one or more separate suspensions of red blood cells, and preferably two of more. The concentration of S-A1c glycated hemoglobin, or S-A1c glycated hemoglobin and acetylated hemoglobin, in each suspension, wherein the concentration is above the normal concentration, is within the ranges set out hereinbefore. Where there are two or more sets of red blood cells in the control, the concentrations of S-A1c glycated hemoglobin, or S-A1c glycated hemoglobin and acetylated hemoglobin, are different in each set. When there are two suspensions having S-A1c glycated hemoglobin, or S-A1c glycated hemoglobin and acetylated hemoglobin, concentrations above the normal range, the concentrations of S-A1c glycated hemoglobin, or S-A1c glycated hemoglobin and acetylated hemoglobin, in the two suspensions are related such that the first has a concentration of greater than 6 to about X and the second has a concentration of greater than X to about 16. X is a real number greater than 6 to 14, preferably from 7 to 10 and most preferably from 8 to 9. In a preferred embodiment, the invention comprises, a cellular hematology control kit for glycated hemoglobin contained in red blood cells comprising a) red blood cells containing from about 4 to about 6 percent by weight of S-A1c glycated hemoglobin based on the total amount of hemoglobin in the red blood cells; b) red blood cells containing from about 7 to about 9 percent by weight of S-A1c glycated hemoglobin, or S-A1c glycated hemoglobin and acetylated hemoglobin, based on the total amount of hemoglobin in the red blood cells and one or more cis di-ahls; and c) red blood cells containing from about 12 to about 14 percent by weight of S-A1c glycated hemoglobin, or S-A1c glycated hemoglobin and acetylated hemoglobin, based on the total amount of hemoglobin in the red blood cells and one or more cis di-ahls. In another preferred embodiment, the invention comprises a cellular hematology control kit for glycated hemoglobin contained in red blood cells comprising a) red blood cells containing from about 4 to about 6 percent by weight of S-A1c glycated hemoglobin based on the total amount of hemoglobin in the red blood cells; and b) red blood cells containing from about 10 to about 12 percent by weight of S-A1c glycated hemoglobin, or S-A1c glycated hemoglobin and acetylated hemoglobin, based on the total amount of hemoglobin in the red blood cells and one or more cis di-ahls. The red blood cells are disposed in a stabilized suspension, preferably an aqueous suspension. In one embodiment of the invention the controls may include the S-A1c glycated hemoglobin, or S-A1c glycated hemoglobin and acetylated hemoglobin without the presence of the cis di-ahls In another embodiment, the invention comprises a method for determining the accuracy and reproducibility of the operation of an analytical instrument capable of measuring the glycated hemoglobin levels comprising
a) providing a cellular hematology control as described herein in a known reference quantity:
b) determining the glycated hemoglobin level in said control of a) with the instrument; and
c) comparing the glycated hemoglobin levels obtained in b) with the known reference quantity.

In certain embodiments, the desired level of S-A1c hemoglobin, S-A1c glycated hemoglobin, or S-A1c glycated hemoglobin and acetylated hemoglobin, is substantially stabilized through adjusting the pH of the control to about 6 to about 8. In yet additional embodiments, the desired level of S-A1c glycated hemoglobin, S-A1c glycated hemoglobin, or S-A1c glycated hemoglobin and acetylated hemoglobin, is substantially maintained through the addition of glucose to the control at an amount of from about 0.001 to about 4 percent by weight. The term substantially stabilized encompasses situations where the S-A1c hemoglobin level of the control varies by no more that about 1 to 2 percent, and preferably, varies by no more than about 1 percent over time. An additional embodiment of the present invention includes a method for determining the accuracy of an analytical instrument capable of measuring S-A1c glycated hemoglobin levels comprising the steps of a) providing a cellular S-A1c hemoglobin control of the present invention in a known reference quantity (e.g. an S-A1c glycated hemoglobin cellular standard); b) determining the level of S-A1c glycated hemoglobin in the control of step a with the instrument; and c) comparing the S-A1c glycated hemoglobin level obtained from step b with the known reference quantity; wherein the comparing indicates the accuracy of said hematology instrument. It will be desirable to obtain a value in step c that is within about 1 to about 5 percent of the value of the known reference quantity. In certain embodiments, the Level 1 cellular glycated S-A1c hemoglobin, S-A1c glycated hemoglobin, or S-A1c glycated hemoglobin and acetylated hemoglobin, controls of the present invention will serve as control or reference standard provided in a known reference quantity of step b, for the normal range of S-A1c glycated hemoglobin levels (S-A1c glycated hemoglobin levels less than or equal to about 6 percent) for use in a variety of diagnostic equipment, including in analytical instrument capable of measuring S-A1c glycated hemoglobin levels. In the compositions and controls of the invention, it is preferable that the concentration of S-A1c glycated hemoglobin, or S-A1c glycated hemoglobin, or S-A1c glycated hemoglobin and acetylated hemoglobin, measured by high pressure liquid chromatography, immunoassay and by boronate affinity methods are consistent and are preferably within a range of about 2 percent and more preferably within a range of about 1 percent. Within a range of 2 percent means that the readings of the various analytical tests are within a range of 2 percent, for example 9.1, 10.0 and 10.9. Although the three methods measure different components of the red blood cells, the software that controls apparatus used to perform the analysis can be adjusted to facilitate consistent results between the two methods.

The control composition is prepared and analyzed by the same standard method as test samples which may be tested in batch quantities by the use of a suitable cassette having apertures for receiving test vials. After preparation, the control composition and test samples are analyzed by detecting the presence of or counting the population number of each subject component type with a multi-parameter automated hematology instrument, which will preferably yield a visual display of the data. In one embodiment the control of the present invention is provided in combination with a peripheral device, such as a device for tracking samples and associating them with particular data, e.g., a bar-code scanner system, an MD system or otherwise. The control may also be provided in combination with a slide preparation kit, stain or dye-resistant labels, lytic reagents (e.g., containing a quaternary ammonium salt), blood diluents, or other like components used in a clinical laboratory setting.

The skilled artisan will appreciate that a number of the steps and ingredients have been disclosed by way of example, but that any of a number of alternative steps or ingredients at the suggested or different parameter or concentration, may be suitably substituted. Though the ingredients or steps have been, in certain instances, described by reference to a particular function or result, it should be appreciated that such discussion is presented without intending to be bound by theory. In some instances, the ingredient or step will perform a different or an additional function or achieve a different result, or multiple other ingredients or steps may be substituted to perform such function or achieve such result. Thus, there is no intention to be bound to the breadth of any specific illustrative step, parameter, ingredient or concentration, where it is apparent that others may be advantageously be employed in addition to or as a substitute.

The present invention is further illustrated by particular reference to the following examples, it being understood that variations of the same may be made while still remaining within the scope of the invention. In the examples that follow, as well as in accordance with the preceding teachings (to which the discussion in this paragraph also applies), it is expected that the resulting cellular components will be capable of detection by an automated hematology analyzer. The resulting sizes of the cellular components may be substantially the same as the starting cells, larger or smaller. When different, the cellular components may range from about one half to about twice the size of the original cells. In certain instances, it is also possible that hemoglobin may be removed from within the cell, with removals (when occurring) ranging from about 0 percent to about 100 percent of the original hemoglobin (e.g., less than about 10 percent, less than about 20 percent, greater than about 70 percent, greater than about 85 percent or otherwise).

SPECIFIC EMBODIMENTS OF THE INVENTION

The following experiments are included to illustrate the invention and are not intended to limit the scope of the claims. All parts and percentages are by weight unless otherwise stated.

General Control Preparation Process

The Red Blood Cells (RBC cells) (stabilized RBC) (hemoglobin (HGB) concentration=12 g/dL, RBC concentration=$4 \times 10^6/\mu L$ and S-A1c=5-6 percent) in stabilizing solution are contacted with carbon monoxide (CO) by bubbling CO through the dispersion of red blood cells. The CO-treated RBC cells are then washed by adding the glycating solution of mannose or glucose and purine compound, 3 percent bovine serum albumin BSA in a glycating medium of phosphate buffer containing phosphate and various antimicrobial agents) as generally described in Table 1, and then the mixture is centrifuged for 15 minutes at 1500 rpm. The glycating solution is then removed by aspirating the supernatant. The washing process is repeated 3 times. The volume of the sample is adjusted such that the hemoglobin concentration is maintained as 11-12 g/dL.

The sample is glycated in a water bath at 37° C. for about 24 hours, glycation step. The hemoglobin concentration is measured at the beginning (0 hr) and at the end (about 22 hours). The sample is allowed to cool to room temperature (RT) for the next step, deglycation.

The glycated samples are washed three times with a diluent solution containing 3 percent bovine serum albumin (BSA) and no mannose, glucose or purine compound. A typical washing procedure includes diluting the sample with diluent, mixing thoroughly and then centrifuging for 15 minutes at 1500 rpm. The supernatant is removed by aspiration. The cell to the diluent ratio is maintained at 1:5. The sample is then deglycated at 30° C. for about 24 hours (glucose glycating agent) or at room temperature where the glycating agent is mannose, de-glycation step.

The deglycated samples are then fixed with 0.005 percent glutaraldehyde in a solution of phosphate buffer (pH 7 with a composition described in the Table 3) at room temperature for 24 hours. The glutaraldehyde amount is calculated based on the RBC concentration of the sample. An equal volume fixing diluent, containing 3 percent BSA and no glucose, is prepared with the calculated amount of the glutaraldehyde. The sample, once fixed with glutaraldehyde, is washed in diluent containing a cis-diahl, the final storing diluent, (detailed composition is provided in Table 4), in order to remove the fixative. The sample is stored at 6° C. for long term storage.

TABLE 4

| Ingredient | diluent | | |
|---|---|---|---|
| | mg % | mM | % |
| EDTA (Na$_2$) | 704 | 18.09 | 0.704 |
| Mg Gluconate | 392 | 9.45 | 0.392 |
| Na$_2$HPO$_4$ | 268 | 18.87 | 0.268 |
| PEG-20k | 700 | 0.35 | 0.700 |
| Inosine | 425 | 15.9 | 0.425 |
| Glucose | 6000 | 333.3 | 6.000 |
| NaOH | 80 | 20 | 0.080 |
| Methylparaben | 40 | 2.6 | 0.040 |
| Neomycin SO$_4$ | 40 | 0.44 | 0.040 |
| Chloramphenicol | 15 | 0.46 | 0.15 |
| Cis di-ahl | 200, 300 or 600 | | 2, 3 or 6 |

The stabilized solutions in the following examples are tested for S-A1c glycated hemoglobin levels. The S-A1c hemoglobin concentrations are measured by HPLC, Immunoassay and Boronate Affinity methods. The HPLC measurement is performed utilizing a A1c 2.2 Plus or G8 Analyzer available from TOSOH Bioscience utilizing manufacturer recommended procedures. The boronate affinity measurement is performed utilizing a Cholestech GDX Analyzer with Cholestech GDX A1c Test Cartridges, available from Cholestech, and Cholestech recommended procedures. The immunoassay testing is performed utilizing a DCA Vantage analyzer, available from Siemens and Siemens recommended procedures.

Examples 1 to 16

Red blood cells are processed as described above adjusting the glucose and catalyst concentration. The final stabilized product contained 3% percent sorbitol. The S-A1c concentrations are measured by HPLC, Immunoassay and Boronate Affinity. The results are compiled in Table 5.

TABLE 5

| | Condition (temp. = 37° C.) | | | Final S-A1c cocn. (%) | | |
|---|---|---|---|---|---|---|
| Example | Glucose | catalyst | catalyst conc. | HPLC | Immunoassay | Affinity |
| 1 | 6% | adenosine | 0.50% | 10.5 | 8.6 | — |
| 2 | | inosine | 0.50% | 10.9 | 10.5 | 8.6 |
| 3 | 6% | inosine | 0.50% | 11.7 | 10.1 | 12.6 |
| 4 | | adenosine | 0.50% | 11.8 | 10.6 | — |
| 5 | 6% | no catalyst | 0.00% | 9.2 | 8.6 | 9.9 |
| 6 | | adenosine | 0.40% | 9.4 | 8.9 | 10.4 |
| 7 | | inosine | 0.20% | 9.8 | 9.3 | 8.5 |

TABLE 5-continued

| | Condition (temp. = 37° C.) | | | Final S-A1c cocn. (%) | | |
|---|---|---|---|---|---|---|
| Example | Glucose | catalyst | catalyst conc. | HPLC | Immunoassay | Affinity |
| 8 | | | 0.40% | 10.3 | 8.6 | 9.1 |
| 9 | | | 0.50% | 9.7 | 9.4 | 9.4 |
| 10 | 6% | inosine | 0.40% | 9.8 | 9.3 | 13.3 |
| 11 | 6% | inosine | 0.40% | 10.4 | 9.5 | 10.4 |
| 12 | 5% | inosine | 0.30% | 9.8 | 8.6 | 8 |
| 13 | | inosine | 0.40% | 9.8 | 8.4 | 8 |
| 14 | 6% | inosine | 0.30% | 9.9 | 9.2 | 9.7 |
| 15 | | inosine | 0.40% | 10 | 8.9 | 10.2 |
| 16 | 6% | inosine | 0.40% | 10.4 | 9.3 | 9.7 |

Table 5 illustrates the impact of sorbitol on the consistency of the standard analytical methods.

Examples 17 to 34

Several samples are prepared using levels of 3 and 6 percent of sorbitol in the stabilized final aqueous suspension. In the preparation of the samples the level and purine catalyst are varied. The glucose concentration in the glycation step is 6 percent and the purine catalyst level in 0.5 percent by weight, except where noted in the glycation suspension. The final aqueous suspensions are tested for S-A1c glycated hemoglobin concentration by boron affinity, high pressure liquid chromatography and immunoassay techniques. The results are compiled in Table 6. Level 1 as used in Table 6 means the diluent as described in Table 4.

TABLE 6

| Example | Catalyst/Concentration | Diluent | S-A1c Affinity | S-A1c Immunoassay | S-A1c HPLC |
|---|---|---|---|---|---|
| 17 | none | Level 1 | 26.8 | 9.6 | 10 |
| 18 | none | Level 1 + Sorbitol 6% | 10.8 | 9.2 | 9.5 |
| 19 | adenosine (0.5) | Level 1 | 20.5 | 8.7 | 11 |
| 20 | adenosine (0.5) | Level 1 + Sorbitol 6% | | 8.6 | 10.5 |
| 21 | guanosine (0.5) | Level 1 | 16.5 | 9.0 | 10.9 |
| 22 | guanosine (0.5) | Level 1 + Sorbitol 6% | 11 | 9.6 | 10.7 |
| 23 | inosine (0.5) | Level 1 | 17.8 | 10.8 | 11.1 |
| 24 | inosine (0.5) | Level 1 + Sorbitol 6% | 8.6 | 10.5 | 10.9 |
| 25 | none | Level 1 | 21.4 | 8.6 | 9.4 |
| 26 | none | Level 1 + Sorbitol 3% | 9.9 | 8.6 | 9.2 |
| 27 | inosine (0.2) | Level 1 | 16.9 | 9.6 | 9.8 |
| 28 | inosine (0.2) | Level 1 + Sorbitol 3% | 8.5 | 9.3 | 9.8 |
| 29 | inosine (0.3) | Level 1 | 16.1 | 9.6 | 10.3 |
| 30 | inosine (0.3) | Level 1 + Sorbitol 3% | 9.1 | 8.6 | 10.3 |
| 31 | inosine (0.5) | Level 1 | 15.9 | 9.7 | 9.7 |
| 32 | inosine (0.5) | Level 1 + Sorbitol 3% | 9.4 | 9.4 | 9.7 |
| 33 | adenosine (0.4) | Level 1 | 20 | 9.3 | 9.6 |
| 34 | adenosine (0.4) | Level 1 + Sorbitol 3% | 10.4 | 8.9 | 9.4 |

Table 6 illustrates the effect of sorbitol on the S-A1c values determined by affinity method.

Examples 35 to 37

Several samples are prepared as described hereinbefore using 2 percent of sorbitol in the stabilized final aqueous suspension. The mannose concentration in the glycation step is 6 percent. The final aqueous suspensions are tested for S-A1c glycated hemoglobin concentration by boron affinity, high pressure liquid chromatography and immunoassay techniques. The results are compiled in Table 7.

TABLE 7

| | S-A1c conc. of the final product | | | |
|---|---|---|---|---|
| Example | Tosoh 2.2 (HPLC) | Tosoh G8 (HPLC) | GDX Cholestech (Affinity) | DCA Vantage (Immunoassay) |
| 35 | 11.7 | 11.1 | 10.2 | 10.9 |
| 36 | No data | 11.2 | 11.2 | 10.5 |
| 37 | 12.1 | 11.7 | 11.2 | 10.7 |

Table 7 illustrates the effect of sorbitol on the S-A1c values determined by affinity method and shows that the results of all three methods are consistent.

General Control Preparation Process

Examples 38 to 78

The Red Blood Cells (RBC cells) (stabilized RBC) (hemoglobin (HGB) concentration=12 g/dL, RBC concentration=$4 \times 10^6$/μL and S-A1c=5-6 percent) in stabilizing solution are contacted with carbon monoxide (CO) by bubbling CO through the dispersion of red blood cells. The CO-treated RBC cells are then washed by adding the glycating solution of 6 percent glucose, 0.4 percent inosine, 3 percent bovine serum albumin BSA in a glycating medium of phosphate buffer containing phosphate and various antimicrobial agents) as generally described in Table 1, and then the mixture is centrifuged for 15 minutes at 1500 rpm. The glycating solution is then removed by aspirating the supernatant. The washing process is repeated 3 times. The volume of the sample is adjusted such that the hemoglobin concentration is maintained as 11-12 g/dL.

The sample is glycated in a water bath at 37° C. for about 24 hours. The hemoglobin concentration is measured at the beginning (0 hr) and at the end (about 22 hours). The sample is allowed to cool to room temperature (RT) for the next step, deglycation. The glycated samples are washed three times with a diluent solution containing 3 percent bovine serum albumin (BSA) and no glucose. A typical washing procedure includes diluting the sample with diluent, mixing thoroughly and then centrifuging for 15 minutes at 1500 rpm. The supernatant is removed by aspiration. The cell to the diluent ratio is maintained at 1:5. The sample is then deglycated at 30° C. for about 24 hours, de-glycation step.

The deglycated samples are then fixed with 0.002 percent glutaraldehyde in a solution of phosphate buffer (pH 7 with a composition described in the Table 3) at room temperature for 24 hours. The glutaraldehyde amount is calculated based on the RBC concentration of the sample. An equal volume fixing diluent, containing 3 percent BSA and no glucose, is prepared with the calculated amount of the glutaraldehyde. The sample, once fixed with glutaraldehyde, is washed in diluent-1, the final storing diluent, detailed composition is provided in Table 4), in order to remove the fixative. The sample is stored at 6° C. for long term storage.

The stabilized solutions in the following examples are tested for S-A1c glycated hemoglobin levels. The S-A1c hemoglobin concentrations are measured by HPLC, Immunoassay and Boronate Affinity methods. The HPLC measurement is performed utilizing a A1c 2.2 Plus Analyzer available from TOSOH Bioscience utilizing manufacturer recommended procedures. The boronate affinity measurement is performed utilizing a Cholestech GDX Analyzer with Cholestech GDX A1c Test Cartridges, available from Cholestech, and Cholestech recommended procedures. The immunoassay testing is performed utilizing a DCA Vantage analyzer, available from Siemens and Siemens recommended procedures.

Examples 38 to 50

Red blood cells are processed as described above with various purine based compounds at 0.4 and 0.5 percent by weight of the glycation suspension. The S-A1c glycated hemoglobin concentrations are measured prior to glycation, after glycation, after deglycation and in the final stabilized solution (final) by Tosoh A1c 2.2 Plus (1-HPLC). The results are compiled in Table 8.

TABLE 8

| | Catalyst | | S-A1c conc. (%) | | | |
|---|---|---|---|---|---|---|
| Example | Name | Conc. (%) | initial | Post-glycation | post-deglycation | final |
| 38 | no catalyst | 0 | 6 | 10 | 10.8 | 11.1 |
| 39 | Inosine | 0.5 | 6 | 11.5 | 12.3 | 11.8 |
| 40 | adenosine* | 0.5 | 6 | 11.1 | 12.1 | 11.7 |
| 41 | guanosine* | 0.5 | 6 | 9.8 | 10.9 | 10.7 |
| 42 | no catalyst | 0 | 6.2 | 8.6 | 9.7 | 9.4 |
| 43 | inosine | 0.4 | 6.2 | 10.6 | 11.3 | 10.3 |
| 44 | adenosine | 0.4 | 6.2 | 10.6 | 11.2 | 9.6 |
| 45 | no catalyst | 0 | 5.5 | 8.4 | 9.4 | 9.2 |
| 46 | inosine | 0.4 | 5.5 | 10.1 | 11.1 | 10.3 |
| 47 | adenosine | 0.4 | 5.5 | 10 | 11 | 9.8 |
| 48 | xanthosine | 0.4 | 5.5 | 9.7 | 10.7 | 9.6 |
| 49 | inosine | 0.4 | 5.5 | 10.4 | 11.6 | Not processed |
| 50 | 2-amino-adenosine* | 0.4 | 5.5 | 9.7 | 11.3 | |

*was not completely soluble at that concentration

Table 8 illustrates effect of purine compounds on the S-A1c synthesis rate.

Examples 51 to 53

Red blood cells are processed as described above using other purine compounds and the S-A1c hemoglobin concentrations are measured by HPLC methods. The results are compiled in Table 9.

TABLE 9

| | Catalyst | | S-A1c conc. (%) | |
|---|---|---|---|---|
| Example | Name | Conc. | initial | Post-glycation |
| 51 | No catalyst | 0 | 6.2 | 8.5 |
| 52 | AMP | 0.5% | 6.2 | 9 |
| 53 | Cyclic AMP | 0.5% | 6.2 | 8.8 |

Table 9 illustrates that presence of one phosphate linkage reduces the catalytic efficiency of the purine derivative.

Examples 54 to 69

Red blood cells are processed as described hereinbefore at various temperatures, 22° C., 30° C. and 37° C. and samples are tested using Tosoh A1c 2.2 Plus (HPLC) test at various times for S-A1c to determine the best temperature to result in the formation of red blood cells having 9 percent by weight of greater S-A1c glycated hemoglobin based on the weight of the hemoglobin. The concentration of glucose in the glycation medium is 6 percent by weight of the glycation medium. The results are compiled in Table 10.

TABLE 10

| | | | S-A1c conc. at different times of glycation | | | |
|---|---|---|---|---|---|---|
| Example | Temp. | A1c | 0 hr | 18 hr | 24 hr | 48 hr |
| 54 | 22° C. | L-A1c | 4.2 | 19.6 | 20.1 | 19.6 |
| 55 | | S-A1c | 6.6 | 6.5 | 6.5 | 6.6 |
| 56 | 30° C. | L-A1c | 4.2 | 19.3 | 19.3 | 18.2 |
| 57 | | S-A1c | 6.6 | 6.6 | 6.6 | 7.1 |
| 58 | 37° C. | L-A1c | 4.2 | 17.4 | 16.6 | 12 |
| 59 | | S-A1c | 6.6 | 7.1 | 7.4 | 9 |
| 60 | 30° C. | L-A1c | 5.1 | 13.6 | 12.4 | 11.3 |
| 61 | | S-A1c | 6.6 | 6.7 | 6.8 | 7.7 |
| 62 | 37° C. | L-A1c | 5.1 | 11.6 | 11.2 | |
| 63 | | S-A1c | 6.6 | 8.5 | 8.9 | |
| 64 | 22° C. | L-A1c | 5.2 | 21.4 | 21.6 | 16 |
| 65 | | S-A1c | 6.6 | 6.5 | 6.5 | 6.7 |
| 66 | 30° C. | L-A1c | 5.2 | 16.8 | 14.7 | 11.8 |
| 67 | | S-A1c | 6.6 | 6.6 | 6.7 | 7.6 |
| 68 | 37° C. | L-A1c | 5.2 | 12.5 | 12.8 | |
| 69 | | S-A1c | 6.6 | 8.2 | 8.6 | |

Table 10 illustrates the effect of temperature on S-A1c synthesis.

Examples 70 to 74

Red blood cells are processed as described above and the S-A1c concentrations are measured by the HPLC (Tosoh A1c 2.2 Plus) method. The BSA concentration is varied. The results are compiled in Table 11.

TABLE 11

| Example | | 5% Glucose + 0.5% inosine | | |
|---|---|---|---|---|
| 70 | BSA Conc. | 3% | 5% | 10% |
| 71 | L-A1c (0 hr) | 2.2 | 2.2 | 2.2 |
| 72 | L-A1c (22 hr) | 8.9 | 8.9 | 8.9 |
| 73 | S-A1c (0 hr) | 6.2 | 6.2 | 6.2 |
| 74 | S-A1c (22 hr) | 10.7 | 10.6 | 10.7 |

Table 11 illustrates that concentration of BSA has no effect on glycation rate.

Examples 75 to 88

Red blood cells are processed as described above and the S-A1c hemoglobin concentrations are measured by HPLC at various times to determine the amount of time needed to achieve a concentration of S-A1c glycated hemoglobin using 6 percent glucose and 0.4 percent inosine at 37° C. The results are compiled in Table 12.

TABLE 12

| | Example | HGB (g/dL) | A1c conc. (%) during glycation | | | | Final A1c conc. (%) |
|---|---|---|---|---|---|---|---|
| | | | 0 | 20 | 21 | 23 | |
| S-A1c | 75 | 9.9 | 6.4 | 9.5 | 9.3 | 9.6 | 10.7 |
| | 76 | 9.6 | 6.3 | 9.1 | 9.1 | 9.6 | 10.4 |
| | 77 | 10.4 | 5.8 | 9 | 8.8 | 9.2 | 10 |
| | 78 | 10.2 | 6.5 | 9.4 | 9.4 | 9.8 | 10.4 |
| | 79 | 9.8 | 6.5 | 9.4 | 9.5 | 9.8 | 10.4 |
| L-A1c | 80 | 9.9 | 5.1 | 9.4 | 9.3 | 9.6 | 5.9 |
| | 81 | 9.6 | 5.1 | 9.3 | 9.2 | 9.4 | 5.9 |
| | 82 | 10.4 | 6 | 9.5 | 9.6 | 9.7 | 5.1 |
| | 83 | 10.2 | 5.3 | 9.1 | 9.2 | 9.4 | 5.5 |
| | 84 | 9.8 | 5.3 | 9.2 | 9.1 | 9.4 | 5.5 |

TABLE 12-continued

| | Example | HGB (g/dL) | A1c conc. (%) during glycation | | | | Final A1c conc. (%) |
|---|---|---|---|---|---|---|---|
| | | | 0 | 20 | 21 | 23 | |
| S-A1c | 85 | 10.7 | 6.6 | 9.9 | 9.9 | 10 | 10.3 |
| | 86 | 11 | 6.6 | 9.8 | 9.9 | 10.2 | 10.4 |
| L-A1c | 87 | 10.7 | 10 | 8.7 | 8.6 | 8.9 | 4.2 |
| | 88 | 11 | 10 | 8.8 | 8.7 | 9 | 4.5 |

Table 12 illustrates the increase in concentration of S-A1c and L-A1c formation with time.

Experimental Process

Examples 89-127

The Red Blood Cells (RBC cells) (stabilized RBC) (hemoglobin (HGB) concentration=12 g/dL, RBC concentration=$4\times10^6$/μL and S-A1c=5-6 percent) in stabilizing solution are contacted with carbon monoxide (CO) by bubbling CO through the dispersion of red blood cells. The CO-treated RBC cells are then washed by adding the glycating solution of 5 percent glucose, 0.25 percent acetyl salicylic acid (ASA), 3 percent bovine serum albumin BSA in a glycating medium of phosphate buffer containing phosphate and various antimicrobial agents) as generally described in Table 1, and then the mixture is centrifuged for 15 minutes at 1500 rpm. The glycating solution is then removed by aspirating the supernatant. The washing process is repeated 3 times. The volume of the sample is adjusted such that the hemoglobin concentration is maintained as 11-12 g/dL. The sample is glycated in a water bath at 37° C. for 20 to 22 hours. The hemoglobin concentration is measured at the beginning (0 hr) and at the end (about 22 hours). The sample is allowed to cool to room temperature (RT) for the next step, deglycation. The glycated samples are washed three times with a diluent solution containing 3 percent bovine serum albumin (BSA) and no glucose. A typical washing procedure includes diluting the sample with diluent, mixing thoroughly and then centrifuging for 15 minutes at 1500 rpm. The supernatant is removed by aspiration. The cell to the diluent ratio is maintained at 1:5. The sample is then deglycated at 30° C. for about 24 hours.

The resulting samples are then fixed with 0.002 percent glutaraldehyde in a solution of phosphate buffer (pH 7 with a composition described in the Table 3) at room temperature for 24 hours. The glutaraldehyde amount is calculated based on the RBC concentration of the sample. An equal volume fixing diluent, containing 3 percent BSA and no glucose, is prepared with the calculated amount of the glutaraldehyde. The sample, once fixed with glutaraldehyde, is washed in diluent-1, the final storing diluent, detailed composition is provided in Table 4), in order to remove the fixative. The sample was stored at 6° C. for long term storage.

Examples 89 to 94

Red blood cells are processed as described above and the S-A1c hemoglobin concentrations are measured by HPLC and Boronate Affinity methods. The HPLC measurement is performed utilizing a A1c 2.2 Plus Analyzer available from TOSOH Bioscience utilizing manufacturer recommended procedures. The boronate affinity measurement is performed utilizing a Cholestech GDX Analyzer with Cholestech GDX A1c Test Cartridges, available from Cholestech, and Cholestech recommended procedures. The results are compiled in Table 13.

TABLE 13

| | Glycation Condition | | | S-A1c conc. (%) | |
|---|---|---|---|---|---|
| Example | Glucose | Temp. | Time | HPLC | Boronate affinity |
| 89 | 6% | 37° C. | 96 hr | 16.9 | 35.7 |
| 90 | 6% | 37° C. | 72 hr | 11.5 | 28.7 |
| 91 | 6% | 37° C. | 48 hr | 11.4 | 23 |
| 92 | 6% | 37° C. | 22 hr | 9.5 | 15 |
| 93 | 5% | 37° C. | 22 hr | 9 | 13.8 |
| 94 | 4% | 37° C. | 22 hr | 8.3 | 9.8 |

Examples 85 to 103

Red blood cells are processed as described above and the S-A1c hemoglobin concentrations are measured by HPLC and Boronate Affinity methods. The concentrations of glucose and acetyl salicylic acid and the incubation times are varied. The results are compiled in Table 14.

TABLE 14

| | Conditions of incubation | | | S-A1c (%) | |
|---|---|---|---|---|---|
| | Glucose | ASA | Time | (after incubation at 37° C.) | |
| Example | (%) | (%) | (hr) | HPLC | Boronate Affinity |
| 95 | 5 | 0.2 | 22.0 | 9.8 | 9.1 |
| 96 | 5 | 0.25 | 22.0 | 10.2 | 10.4 |
| 97 | 5 | 0.3 | 15 | 10.2 | 11.3 |
| 98 | 5 | 0.3 | 22.0 | 10.6 | 9.8 |
| 99 | 5 | 0.4 | 5.5 | 9.9 | 6.7 |
| 100 | 6 | 0.2 | 15 | 9.4 | 10.3 |
| 101 | 6 | 0.3 | 15 | 10.3 | 12.5 |
| 102 | 10 | 0.2 | 22.0 | 10.8 | 13.6 |
| 103 | 10 | 0.4 | 5.5 | 9.3 | 6.4 |

Table 14 illustrates that the right combination of the concentrations of glucose and the acetylating agent, ASA, is important to maintain an accelerated incubation process and to obtain an equal value of S-A1c hemoglobin concentration measured as measured by HPLC and boron affinity methods. In these examples, the S-A1c hemoglobin concentration of a sample, obtained by this procedure, determined by HPLC, is the concentration of the combined glycated hemoglobin and acetylated hemoglobin. Therefore, the HPLC reported value is referred as S-A1c peak area. On the other hand, S-A1c concentration determined by the boronate affinity method is solely due to the glycated hemoglobin. Thus, the boronate affinity method reported value is referred as S-A1c concentration. In general, the S-A1c concentrations, reported by different methods, are referred as S-A1c value. The higher concentration of glucose during incubation, at a given ASA concentration, increases the rate of the S-A1c synthesis and the values of S-A1c concentration reported by both of the HPLC and boronate affinity methods. The S-A1c values measured by the boronate affinity method are increased many fold because of the increase in concentrations of the minor components. The higher concentration of ASA, on the other hand, increases the S-A1c peak area in HPLC and the rate at which the increase occurs. However, the S-A1c value reported by the boronate affinity method is found to decrease with higher ASA at a constant glucose concentration. Higher (≥6 percent) glucose concentrations caused hemolysis. Therefore, 5-6 percent is the optimum glucose concentration. Incubation with 0.3 percent ASA provides a sample with the most reproducible value of S-A1c concentration. (Acetylation produces many transiently stable acetylated-hemoglobin species which may contribute to the fluctuating S-A1c concentration values.)

Examples 104 to 117

Red blood cells are processed as described above and the S-A1c concentrations are measured by HPLC and Boronate Affinity. The concentration of acetyl salicylic acid is varied. The results are compiled in Table 15.

TABLE 15

| | Conditions of incubation | | S-A1c (%) | |
|---|---|---|---|---|
| Example | Glucose (%) | ASA (%) | HPLC | Affinity |
| 104 | 5 | 0.2 | 10.2 | 8.6 |
| 105 | 5 | 0.2 | 10.2 | 13.8 |
| 106 | 5 | 0.2 | 11.1 | 12.1 |
| 107 | 5 | 0.2 | 10.4 | 8.6 |
| 108 | 5 | 0.3 | 10.8 | 10.7 |
| 109 | 5 | 0.3 | 10.6 | 10.6 |
| 110 | 5 | 0.3 | 10.9 | 12.1 |
| 111 | 5 | 0.3 | 11.7 | 11.3 |
| 112 | 5 | 0.4 | 11.4 | 11.8 |
| 113 | 6 | 0.2 | 10.4 | na |
| 114 | 6 | 0.3 | 11.1 | 12.2 |
| 115 | 7 | 0.2 | 10.7 | 14.5 |
| 117 | 7 | 0.3 | 11.5 | 11.4 |
| 118 | 7 | 0.4 | 11.9 | 7.1 |

The deglycation of RBC erythrocytes with 5 to 6 percent glucose combined with 0.2 to 0.3 percent ASA at 37° C. for 24 hr results in an increase of S-A1c concentration values from 5 to 6 percent range to the 9 to 10 percent range. The preferred condition are 5 percent glucose with 0.3 percent ASA.

Examples 119 to 121

Red blood cells are processed as described above and the S-A1c concentrations are measured by HPLC and Boronate Affinity methods. The ratio of glucose to hemoglobin is varied. In order to obtain a desired target concentration of S-A1c in a range of 10□ to 11 percent, the hemoglobin concentration (HGB) is maintained in the 11-12 g/dL range. The results are compiled in Table 16.

TABLE 16

| | Sample | 1 mol of glucose + 0.04 mol of ASA | | 37° C. | |
|---|---|---|---|---|---|
| | HGB conc. | HGB | RBC | after 15 hr | |
| Example | (g/dL) | (×10⁻³ mol) | (×10¹² mol) | L-A1c | S-A1c |
| 119 | 8.9 | 4.96 | 9.9 | 11.5 | 10.8 |
| 120 | 12.6 | 7.01 | 13.74 | 11.1 | 10.1 |
| 121 | 16.7 | 9.32 | 18.13 | 10.7 | 9.6 |

Examples 122 to 127

Red blood cells are processed as described above and the S-A1c hemoglobin concentrations are measured by HPLC and Boronate Affinity. The deglycation is performed with 5 percent glucose, 0.25 percent by weight acetyl salicylic acid at 37° C. The results are compiled in Table 17.

TABLE 17

| Reaction time (hr) | | 0 | 15 | 20 | 24 | 30 |
|---|---|---|---|---|---|---|
| S-A1c | Example 124 | 6.3 | 8.6 | 8.7 | 9.3 | 9.6 |
| | Example 125 | 6.2 | 8.3 | 8.5 | 9.1 | 9.4 |
| L-A1c | Example 126 | 6.3 | 7.1 | 7 | 7.1 | 6.9 |
| | Example 127 | 6.3 | 7.2 | 7.1 | 7.1 | 6.9 |

The reaction time is determined based on the desired target (post glycation stage) of S-A1c concentration. In order to obtain about 9-10 percent S-A1c concentration of the final product, the glycation is stopped at about 20-22 hours when the S-A1c concentration is about 9-10 percent.

It will be appreciated that concentrates or dilutions of the amounts recited herein may be employed. In general, the relative proportions of the ingredients recited will remain the same. Thus, by way of example, if the teachings call for 30 parts by weight of a Component A, and 10 parts by weight of a Component B, the skilled artisan will recognize that such teachings also constitute a teaching of the use of Component A and Component B in a relative ratio of 3:1.

It will be appreciated that the above is by way of illustration only. Other ingredients may be employed in any of the compositions disclosed herein, as desired, to achieve the desired resulting characteristics. Examples of other ingredients that may be employed include antibiotics, anesthetics, antihistamines, preservatives, surfactants, antioxidants, unconjugated bile acids, mold inhibitors, nucleic acids, pH adjusters, osmolarity adjusters, or any combination thereof. Specific examples of ingredients that may be employed include one or more of sodium fluoride, a paraben (e.g., propyl), sulfasalazine, sodium phosphate, potassium phosphate, sodium citrate, citric acid, sodium chloride, bovine serum albumin, sodium hydroxide, lipoprotein, Proclin, adenine, mannose, dextrose, lactose, penicillin, tetracycline, promethazine, a purine (e.g., adenine), inosine, kanamycin sulfate, cyclohexamide, deoxycholic acid, colistimethate sodium, trisodium citrate dehydrate, 5-Fluorouracil, or any combination thereof.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A storage stable control composition for determining glycosylated or acetylated hemoglobin comprising:
   intact red blood cells in a suspension medium; and
   an effective amount of one or more of sorbitol, fructose, and mannitol effective to provide for consistent results when measuring hemoglobin that is glycated or acetylated or both as determined by HPLC, immunoassay, or boron affinity methods of analysis;
   wherein more than about 6 percent by weight of the hemoglobin in the intact red blood cells is S-A1c glycated; and
   wherein the intact red blood cells' membranes are preserved and strengthened so that the intact red blood cells resist hemoglobin leakage for a storage period of at least about 4 months or longer.

2. The composition of claim 1 wherein the suspension medium is an aqueous suspension medium.

3. The composition of claim 1 further comprising from about 0.3 to about 0.6 percent by weight of glucose based on the weight of the composition.

4. The composition of claim 1 wherein the effective amount of one or more of sorbitol, fructose, and mannitol is between about 1 and about 6 percent by weight based on the weight of the composition.

5. The composition of claim 1 wherein the source of the red blood cells is a non-diabetic human.

6. The composition of claim 1 wherein the concentration of S-A1c glycated hemoglobin measured by high pressure liquid chromatography, immunoassay and boronate affinity methods are within a range of units of about 2 percent.

7. A cellular hematology control for measuring glycated hemoglobin in intact red blood cells comprising:
   intact red blood cells having a predetermined level of S-A1c glycated hemoglobin, said predetermined level being greater than about 6 percent by weight of the S-A1c glycated hemoglobin to non-S-A1c glycated hemoglobin; and
   an effective amount of one or more of sorbitol, fructose, and mannitol in a stabilized suspension medium, effective to provide for consistent results when measuring hemoglobin that is glycated or acetylated or both as determined by HPLC, immunoassay, or boron affinity methods of analysis;
   wherein the intact red blood cells' membranes are preserved and strengthened so that the intact red blood cells resist hemoglobin leakage for a storage period of at least about 4 months or longer; and
   wherein the source of the intact red blood cells is a healthy, non-diabetic human so that the intact red blood cells are free from interfering abnormal hemoglobin variants.

8. The cellular hematology control of claim 7 wherein the effective amount of one or more of sorbitol, fructose, and mannitol is between about 1 and about 6 percent by weight based on the weight of the composition.

9. A cellular hematology control kit for determining glycated hemoglobin comprising at least components (a), (b), and (c):
   a) a first solution of intact red blood cells in a stabilized aqueous medium wherein the hemoglobin contains from about 4 to about 6 percent by weight of S-A1c glycated hemoglobin based on the weight of the hemoglobin; and
   b) a second solution of intact red blood cells in a stabilized aqueous medium wherein the hemoglobin contains greater than about 6 and less than or equal to about X percent by weight of S-A1c glycated hemoglobin based on the weight of the hemoglobin; and
   about 1 and about 6 percent by weight of one or more of sorbitol, fructose, and mannitol based on the weight of the stabilized aqueous medium; and
   c) a third solution of intact red blood cells in a stabilized aqueous medium wherein the hemoglobin contains greater than or equal to about X and less than about 14 percent by weight of S-A1c glycated hemoglobin based on the weight of the hemoglobin; and
   about 1 and about 6 percent by weight of one or more of sorbitol, fructose, and mannitol based on the weight of the stabilized aqueous medium;
   wherein X is a value between 7 and 14;
   wherein the intact red blood cells' membranes are preserved and strengthened so that the intact red blood cells resist hemoglobin leakage for a storage period of at least about 4 months or longer.

10. The hematology control kit of claim 9 where the source of the intact red blood cells is a healthy, non-diabetic human wherein the intact red blood cells are free from interfering abnormal hemoglobin variants.

11. The composition of claim 1 further comprising:
a portion of the hemoglobin is acetylated or S-A1c glycated hemoglobin or both;
wherein acetylation or S-A1c glycation occurs on the terminal valine amino acid of the alpha or beta chain of the hemoglobin; and
wherein more than 6 percent by weight of the hemoglobin is acetylated or glycated on said terminal valine.

12. The cellular hematology control of claim 7 wherein the control is capable of testing multiple elements of a blood sample which may include various white blood cell populations, nucleated red blood cells, reticulocytes, or other blood cell types.

13. The composition of claim 1 wherein the intact red blood cells used to synthesize the composition are stabilized intact red blood cells.

14. The composition of claim 1 wherein the one or more of sorbitol, fructose, and mannitol is cell impermeable so that the cell volume of the intact red blood cells is not increased.

15. The composition of claim 1 wherein the control further comprises an addition of glucose so that the desired level of S-A1c hemoglobin is maintained; wherein the amount of the addition of glucose is about 0.001 to about 4 percent by weight.

16. The composition of claim 1 wherein the intact blood cells' membranes are preserved and strengthened by a fixing compound, and wherein the fixing compound is one or more of an aldehyde, oxazolidine, alcohol, cyclic urea, or combinations thereof.

17. The composition of claim 1 wherein the fixing compound is glutaraldehyde.

18. The composition of claim 1 wherein the suspension medium contains glucose and a compound containing a purine ring structure having a ribose sugar ligand attached to the five membered ring of the purine ring structure at about 35° C. to about 40° C.

* * * * *